US007319034B2

(12) United States Patent
Noteborn et al.

(10) Patent No.: US 7,319,034 B2

(45) Date of Patent: Jan. 15, 2008

(54) MODIFICATIONS OF APOPTIN

(75) Inventors: Mathieu Hubertus Maria Noteborn, Leiderdorp (NL); Jennifer Leigh Rohn, Amsterdam (NL); Dominik Mumberg, Berlin (DE); Peter Donner, Berlin (DE)

(73) Assignee: Leadd B.V., Leiden (NL)

( * ) Notice: Subject to any disclaimer, the term of this patent is extended or adjusted under 35 U.S.C. 154(b) by 654 days.

(21) Appl. No.: 10/083,849

(22) Filed: Oct. 19, 2001

(65) Prior Publication Data

US 2003/0199009 A1 Oct. 23, 2003

Related U.S. Application Data

(60) Provisional application No. 60/242,397, filed on Oct. 20, 2000.

(30) Foreign Application Priority Data

Oct. 20, 2000 (EP) .................................. 00203652

(51) Int. Cl.
*C12N 15/85* (2006.01)

(52) U.S. Cl. .................................... 435/366; 435/320.1

(58) Field of Classification Search ............. 435/320.1, 435/325, 419, 243
See application file for complete search history.

(56) References Cited

U.S. PATENT DOCUMENTS 5,491,073 A 2/1996 Noteborn et al.

FOREIGN PATENT DOCUMENTS

| | | | |
|---|---|---|---|
| WO | WO9503414 | * | 2/1995 |
| WO | WO 96/41191 | | 12/1996 |
| WO | WO 98/46740 | | 10/1998 |
| WO | WO 99/08108 | | 2/1999 |
| WO | WO 99/28461 | | 6/1999 |

* cited by examiner

*Primary Examiner*—James Ketter
(74) *Attorney, Agent, or Firm*—TraskBritt

(57) ABSTRACT

Phosphorylated Apoptin is described. Apoptin is tumor-specifically phosphorylated and part of the Apoptin apoptotic pathway in tumor cells is elucidated. New therapeutic possibilities, for example, novel therapeutic compounds that can work alone or, sequentially to, or jointly with other known compounds. Also, the use of tumor-specifically phosphorylation of Apoptin for diagnostic purposes is described. Such a diagnostic purpose can, for example, be a method for detecting the presence of cancer cells or cells that are cancer prone or a method to identify a putative cancer inducing agent or a method for the in vitro treatment effect of Apoptin on tumor cells by testing the phosphorylation state of Apoptin. Even more, the invention provides possibilities to further elucidate the apoptotic pathway and to identify for example crucial mediators of phosphorylation in human tumor cells. Interfering with such a mediator could provide new anti-cancer therapies.

7 Claims, 4 Drawing Sheets

SEQUENCE LISTING

```
<160> NUMBER OF SEQ ID NOS: 20

<210> SEQ ID NO 1
<211> LENGTH: 121
<212> TYPE: PRT
<213> ORGANISM: Chicken anemia virus
<220> FEATURE:
<221> NAME/KEY: MISC_FEATURE
<222> LOCATION: (1)..(121)
<223> OTHER INFORMATION: Apoptin (a small protein derived from chicken
      anemia virus) encoded by pCMV-Vp3 and by GFP-Apoptin constructs

<400> SEQUENCE: 1

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Thr Thr Thr Pro Ser Arg Pro
            100                 105                 110

Arg Thr Ala Arg Arg Arg Ile Arg Leu
        115                 120


<210> SEQ ID NO 2
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: Apoptin protein encoded by pIRESneo alanine
      mutants
<220> FEATURE:
<221> NAME/KEY: MISC_FEATURE
<223> OTHER INFORMATION: Differs from Apoptin protein encoded by
      pCMV-Vp3 and by GFP-Apopt in constructs by replacement of the
      arginine residue at position 116 with a lysine residue

<400> SEQUENCE: 2

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60
```

-continued

```
Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Thr Thr Thr Pro Ser Arg Pro
            100                 105                 110

Arg Thr Ala Lys Arg Arg Ile Arg Leu
        115                 120


<210> SEQ ID NO 3
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: mutant Ala(5)-86 of 5-alanine linker-scanning
      mutant series of Apoptin

<400> SEQUENCE: 3

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Ala Ala Ala Ala Ala Asp Pro Ser Glu Tyr Arg
                85                  90                  95

Val Ser Glu Leu Lys Glu Ser Leu Ile Thr Thr Thr Pro Ser Arg Pro
            100                 105                 110

Arg Thr Ala Arg Arg Arg Ile Arg Leu
        115                 120


<210> SEQ ID NO 4
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: mutant Ala(5)-91 of 5-alanine linker-scanning
      mutant series of Apoptin

<400> SEQUENCE: 4

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Ala Ala Ala Ala Ala Arg
```

-continued

```
                85                  90                  95

Val Ser Glu Leu Lys Glu Ser Leu Ile Thr Thr Thr Pro Ser Arg Pro
            100                 105                 110

Arg Thr Ala Arg Arg Arg Ile Arg Leu
        115                 120


<210> SEQ ID NO 5
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: mutant Ala(5)-96 of 5-alanine linker-scanning
      mutant series of Apoptin

<400> SEQUENCE: 5

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Ala
                85                  90                  95

Ala Ala Ala Ala Lys Glu Ser Leu Ile Thr Thr Thr Pro Ser Arg Pro
            100                 105                 110

Arg Thr Ala Arg Arg Arg Ile Arg Leu
        115                 120


<210> SEQ ID NO 6
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: mutant Ala(5)-101 of 5-alanine linker-scanning
      mutant series of Apoptin

<400> SEQUENCE: 6

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Ala Ala Ala Ala Ala Thr Thr Thr Pro Ser Arg Pro
            100                 105                 110
```

```
Arg Thr Ala Arg Arg Arg Ile Arg Leu
        115                 120


<210> SEQ ID NO 7
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: mutant Ala(5)-106 of 5-alanine linker-scanning
      mutant series of Apoptin

<400> SEQUENCE: 7

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Ala Ala Ala Ala Ala Arg Pro
            100                 105                 110

Arg Thr Ala Arg Arg Arg Ile Arg Leu
        115                 120


<210> SEQ ID NO 8
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: mutant Ala(5)-111 of 5-alanine linker-scanning
      mutant series of Apoptin

<400> SEQUENCE: 8

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Thr Thr Thr Pro Ser Ala Ala
            100                 105                 110

Ala Ala Ala Arg Arg Arg Ile Arg Leu
        115                 120


<210> SEQ ID NO 9
```

-continued

<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: mutant Ala(5)-116 of 5-alanine linker-scanning mutant series of Apoptin

<400> SEQUENCE: 9

```
Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Thr Thr Thr Pro Ser Arg Pro
            100                 105                 110

Arg Thr Ala Ala Ala Ala Ala Ala Leu
        115                 120
```

<210> SEQ ID NO 10
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: single point mutant T106A of Apoptin

<400> SEQUENCE: 10

```
Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Ala Thr Thr Pro Ser Arg Pro
            100                 105                 110

Arg Thr Ala Arg Arg Arg Ile Arg Leu
        115                 120
```

<210> SEQ ID NO 11
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)

-continued

<223> OTHER INFORMATION: single point mutant T107A of Apoptin

<400> SEQUENCE: 11

```
Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Thr Ala Thr Pro Ser Arg Pro
            100                 105                 110

Arg Thr Ala Arg Arg Arg Ile Arg Leu
        115                 120
```

<210> SEQ ID NO 12
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: single point mutant T108A of Apoptin

<400> SEQUENCE: 12

```
Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Thr Thr Ala Pro Ser Arg Pro
            100                 105                 110

Arg Thr Ala Arg Arg Arg Ile Arg Leu
        115                 120
```

<210> SEQ ID NO 13
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: single point mutant P109A of Apoptin

<400> SEQUENCE: 13

```
Met Asn Ala Leu Gln Glu Asp Thr Pro Pro Gly Pro Ser Thr Val Phe
1               5                   10                  15
```

-continued

```
Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Thr Thr Thr Ala Ser Arg Pro
            100                 105                 110

Arg Thr Ala Arg Arg Arg Ile Arg Leu
        115                 120


<210> SEQ ID NO 14
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: single point mutant T106E of Apoptin

<400> SEQUENCE: 14

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Glu Thr Thr Pro Ser Arg Pro
            100                 105                 110

Arg Thr Ala Arg Arg Arg Ile Arg Leu
        115                 120


<210> SEQ ID NO 15
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: single point mutant T107E of Apoptin

<400> SEQUENCE: 15

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
```

-continued

```
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Thr Glu Thr Pro Ser Arg Pro
            100                 105                 110

Arg Thr Ala Arg Arg Arg Ile Arg Leu
        115                 120


<210> SEQ ID NO 16
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: single point mutant T108E of Apoptin

<400> SEQUENCE: 16

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Thr Thr Glu Pro Ser Arg Pro
            100                 105                 110

Arg Thr Ala Arg Arg Arg Ile Arg Leu
        115                 120


<210> SEQ ID NO 17
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: double point mutation T106A107A of Apoptin

<400> SEQUENCE: 17

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95
```

-continued

Val Ser Glu Leu Lys Glu Ser Leu Ile Ala Ala Thr Pro Ser Arg Pro
100 105 110

Arg Thr Ala Arg Arg Arg Ile Arg Leu
115 120

<210> SEQ ID NO 18
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: double point mutant T107A108A of Apoptin

<400> SEQUENCE: 18

Met Asn Ala Leu Gln Glu Asp Thr Pro Pro Gly Pro Ser Thr Val Phe
1 5 10 15

Arg Pro Pro Thr Ser Ser Arg Pro Leu Glu Thr Pro His Cys Arg Glu
20 25 30

Ile Arg Ile Gly Ile Ala Gly Ile Thr Ile Thr Leu Ser Leu Cys Gly
35 40 45

Cys Ala Asn Ala Arg Ala Pro Thr Leu Arg Ser Ala Thr Ala Asp Asn
50 55 60

Ser Glu Ser Thr Gly Phe Lys Asn Val Pro Asp Leu Arg Thr Asp Gln
65 70 75 80

Pro Lys Pro Pro Ser Lys Lys Arg Ser Cys Asp Pro Ser Glu Tyr Arg
85 90 95

Val Ser Glu Leu Lys Glu Ser Leu Ile Thr Ala Ala Pro Ser Arg Pro
100 105 110

Arg Thr Ala Arg Arg Arg Ile Arg Leu
115 120

<210> SEQ ID NO 19
<211> LENGTH: 121
<212> TYPE: PRT
<213> ORGANISM: Chicken anemia virus
<220> FEATURE:
<221> NAME/KEY: MUTAGEN
<222> LOCATION: (1)..(121)
<223> OTHER INFORMATION: double point mutant T106A108A of Apoptin

<400> SEQUENCE: 19

Met Asn Ala Leu Gln Glu Asp Thr Pro Pro Gly Pro Ser Thr Val Phe
1 5 10 15

Arg Pro Pro Thr Ser Ser Arg Pro Leu Glu Thr Pro His Cys Arg Glu
20 25 30

Ile Arg Ile Gly Ile Ala Gly Ile Thr Ile Thr Leu Ser Leu Cys Gly
35 40 45

Cys Ala Asn Ala Arg Ala Pro Thr Leu Arg Ser Ala Thr Ala Asp Asn
50 55 60

Ser Glu Ser Thr Gly Phe Lys Asn Val Pro Asp Leu Arg Thr Asp Gln
65 70 75 80

Pro Lys Pro Pro Ser Lys Lys Arg Ser Cys Asp Pro Ser Glu Tyr Arg
85 90 95

Val Ser Glu Leu Lys Glu Ser Leu Ile Ala Thr Ala Pro Ser Arg Pro
100 105 110

Arg Thr Ala Arg Arg Arg Ile Arg Leu
115 120

-continued

```
<210> SEQ ID NO 20
<211> LENGTH: 8
<212> TYPE: PRT
<213> ORGANISM: Chicken anemia virus
<220> FEATURE:
<221> NAME/KEY: MISC_FEATURE
<223> OTHER INFORMATION: amino acid sequence encoding the SV40-Large T
      nuclear localization signal

<400> SEQUENCE: 20

Pro Pro Lys Lys Lys Arg Lys Val
1               5
```

MODIFICATIONS OF APOPTIN

CROSS-REFERENCE TO RELATED APPLICATIONS

Under the provisions of 35 U.S.C. § 119(e), priority is claimed from provisional patent application Ser. No. 60/242,397, filed Oct. 20, 2000.

TECHNICAL FIELD

The invention relates generally to physiological chemistry and biotechnology and, more specifically, to the apoptotic pathway induced by Apoptin in tumor cells.

BACKGROUND

Apoptosis is an active and programmed physiological process for eliminating superfluous, altered or malignant cells (Earnshaw, 1995; Duke et al., 1996). The terms "transformed" and "tumorigenic" will be used interchangeably herein. Apoptosis is characterized by shrinkage of cells, segmentation of the nucleus, and condensation and cleavage of DNA into domain-sized fragments, in most cells followed by internucleosomal degradation. The apoptotic cells fragment into membrane-enclosed apoptotic bodies. Finally, neighboring cells and/or macrophages will rapidly phagocytose these dying cells (Wyllie et al., 1980; White, 1996). Cells grown under tissue-culture conditions and cells from tissue material can be analyzed for being apoptotic with DNA-staining agents, such as, e.g., DAPI, which stains normal DNA strongly and regularly, whereas apoptotic DNA is stained weakly and/or irregularly (Noteborn et al., 1994; Telford et al., 1992).

The apoptotic process can be initiated by a variety of regulatory stimuli (Wyllie, 1995; White 1996; Levine, 1997). Changes in the cell survival rate play an important role in human pathogenesis of diseases, e.g., in cancer development and autoimmune diseases, where enhanced proliferation or decreased cell death (Kerr et al., 1994; Paulovich, 1997) is observed. A variety of chemotherapeutic compounds and radiation have been demonstrated to induce apoptosis in tumor cells, in many instances, via wild-type p53 protein (Thompson, 1995; Bellamy et al., 1995; Steller, 1995; McDonell et al., 1995).

Many tumors, however, acquire a mutation in p53 during their development, often correlating with poor response to cancer therapy. Certain transforming genes of tumorigenic DNA viruses can inactivate p53 by directly binding to it (Teodoro, 1997). An example of such an agent is the large T antigen of the tumor DNA virus SV40. For several (leukemic) tumors, a high expression level of the proto-oncogene Bcl-2 or Bcr-ab1 is associated with a strong resistance to various apoptosis-inducing chemotherapeutic agents (Hockenberry, 1994; Sachs and Lotem, 1997).

For such tumors lacking functional p53 (representing more than half of the tumors), alternative anti-tumor therapies are under development based on induction of apoptosis independent of p53 (Thompson, 1995; Paulovich et al., 1997). For this, one has to search for the factors involved in induction of apoptosis that do not need p53 and/or cannot be blocked by anti-apoptotic activities, such as Bcl-2 or Bcr-ab1-like ones. These factors might be part of a distinct apoptosis pathway or might be (far) downstream of the apoptosis-inhibiting compounds.

Apoptin (also called "Vp3", the terms being used interchangeably herein) is a small protein derived from chicken anemia virus (CAV; Noteborn and De Boer, 1996; Noteborn et al., 1991; Notebom et al., 1994; 1998a), which induces apoptosis in human malignant and transformed cell lines, but not in untransformed human cell cultures. In vitro and in vivo, Apoptin fails to induce apoptosis in normal lymphoid, dermal, epidermal, endothelial and smooth-muscle cells. However, when normal cells are transformed, they become susceptible to apoptosis by Apoptin. Long-term expression of Apoptin in normal human fibroblasts revealed that Apoptin has no toxic or transforming activity in these cells (Danen-van Oorschot, 1997; and Noteborn, 1996).

In normal cells, Apoptin was found predominantly in the cytoplasm, whereas in transformed or malignant cells, i.e., characterized by hyperplasia, metaplasia or dysplasia, it was located in the nucleus, suggesting that the localization of Apoptin is related to its activity (Danen-van Oorschot et al. 1997).

Apoptin-induced apoptosis occurs in the absence of functional p53 (Zhuang et al., 1995a) and cannot be blocked by Bcl-2, Bcr-ab1 (Zhuang et al., 1995), or the Bcl-2-associating protein BAG-1 (Danen-Van Oorschot, 1997a; Notebom, 1996).

Therefore, Apoptin is a therapeutic compound for the selective destruction of tumor cells, or other hyperplasia, metaplasia or dysplasia, especially for those tumor cells that have become resistant to (chemo-)therapeutic induction of apoptosis, due to the lack of functional p53 and (over-)expression of Bcl-2 and other apoptosis-inhibiting lesions (Noteborn and Pietersen, 1999). It appears that even pre-malignant, minimally transformed cells are sensitive to the death-inducing effect of Apoptin. In addition, Noteborn and Zhang (1998) have shown that Apoptin-induced apoptosis is suitable for the diagnosis and treatment of cancer-prone cells.

The fact that Apoptin does not induce apoptosis in normal human cells implies that there would be little or no toxic effect of Apoptin treatment in vivo. Noteborn and Pietersen (1998) and Pietersen et al. (1999) have provided evidence that adenovirus-expressed Apoptin does not have a toxic effect in vivo. In addition, in nude mice it was shown that Apoptin has a strong antitumor activity.

SUMMARY OF THE INVENTION

To further enlarge the array of therapeutic anti-cancer or anti-autoimmune disease compounds available in the art, additional therapeutic compounds are desired, especially in those cases wherein p53 is (partly) nonfunctional.

The invention hereof provides an isolated or recombinant phosphorylated Apoptin or functional equivalent and/or functional fragment thereof. Preferably, the Apoptin is tumor-specifically phoshorylated. More preferably, the Apoptin is phosphorylated on a threonine residue, which residue in the Apoptin depicted in FIG. 1 is located between amino acid 100 and 121. Most preferably, Apoptin is phosphorylated on a threonine residue, which residue in the Apoptin of FIG. 1 is located at amino acid 106 and/or 107 and/or 108. "Functional equivalent" and/or "functional fragment thereof" are herein defined as Apoptin and/or part thereof, optionally coupled to other components, wherein phosphorylation is according to the invention or wherein phosphorylation is mimicked by, for example, introducing a negative charge which mimics the negative charge of phosphate or wherein the effect of phosphorylation is obtained by other methods known in the art, for example, chemical crosslinking of phosphate or phosphate mimics to Apoptin. An example of a functional equivalent is a single point mutation of, for example, amino acid 107 from threonine to glutamic acid as depicted in FIG. 4 and described in the detailed experimental part herein. An example of a functional fragment, which in this case is coupled to another component, is GFP-deletion mutant GFP-70-121 as depicted in FIG. 2 and described in the detailed description herein. The fact that Apoptin phosphorylated, according to the invention and, even more, is tumor-specifically phosphorylated, discloses part of the apoptotic pathway as induced by Apoptin in tumor cells and opens the way to, for example, further elucidation of the apoptotic pathway induced by Apoptin in tumor cells, identification of crucial mediators of phosphorylation in human tumor cells, new diagnostic assays or new pharmaceutical compounds.

In another embodiment, the invention provides a vector encoding Apoptin or functional equivalent and/or functional fragment thereof, which can be phosphorylated and, furthermore, the vector also comprises a nucleic acid molecule encoding a kinase capable of phosphorylating the Apoptin or functional equivalent and/or functional fragment according to the invention.

In yet another embodiment, the invention provides a gene delivery vehicle comprising a vector according to the invention which enables using Apoptin or a functional equivalent and/or functional fragment thereof which can be phosphorylated for cancer treatment via the use of gene-therapy. By equipping a gene delivery vehicle with a nucleic acid molecule encoding Apoptin or functional equivalent and/or functional fragment thereof, and by further providing a nucleic acid molecule encoding a kinase capable of phosphorylating the Apoptin or functional equivalent and/or functional fragment thereof according to the invention, and by targeting the vehicle to a cell or cells that show over-proliferating behavior and/or have shown decreased death rates, the gene delivery vehicle provides the cell or cells with the necessary means of apoptosis, providing therapeutic possibilities.

Furthermore, the invention provides a host cell comprising a vector or a gene delivery vehicle encoding Apoptin or functional equivalent and/or functional fragment thereof, which can be phosphorylated according to the invention. Not all host cells comprising this vector are capable of protein phosphorylation and, by further providing the vector with a nucleic acid encoding a kinase, Apoptin is phosphorylated according to the invention.

The invention also provides an isolated or synthetic antibody or functional equivalent and/or functional fragment thereof specifically recognizing phosphorylated Apoptin according to the invention. Such an antibody is, for example, obtainable by immunizing an immuno-competent animal with phosphorylated Apoptin or an immunogenic fragment or equivalent thereof and harvesting polyclonal antibodies from the immunized animal, or obtainable by other methods known in the art such as by producing monoclonal antibodies, or (single chain) antibodies or binding proteins expressed from recombinant nucleic acid derived from a nucleic acid library, for example, obtainable via phage display techniques. Phosphospecific antibodies are routinely generated, and, in most cases, an antibody is developed that recognizes the phosphorylated epitope of the protein of interest, but not the non-phosphorylated version (Blaydes et al., 2000).

With such an antibody, the invention also provides an immunoassay comprising an antibody according to the invention. A lot of immunoassays are available within the art, for example, ELISA (Enzyme Linked Immuno Sorbent Assay) or Western blotting.

Furthermore, the invention provides use of Apoptin or functional fragment thereof which can be phosphorylated according to the invention for diagnostic purposes. One embodiment of a diagnostic assay is a method for detecting the presence of cancer cells or cells that are cancer prone in a sample of cells comprising providing a cell lysate of the cells with Apoptin or functional equivalent and/or functional fragment thereof which can be phosphorylated according to the invention and determining the phosphorylation state of the Apoptin.

Another embodiment of a diagnostic assay is a method for identifying a putative cancer-inducing agent comprising submitting a sample of cells to the agent and detecting the presence of cancer cells, or cells that are cancer prone, in a sample of cells comprising providing a cell lysate of the cells with Apoptin or functional equivalent and/or functional fragment thereof which can be phosphorylated according to the invention and determining the phosphorylation state of the Apoptin.

Another embodiment of a diagnostic assay is a method for testing the in vitro treatment effect of Apoptin on tumor cells comprising submitting a cell lysate of the tumor cells to the Apoptin or functional fragment thereof which can be phosphorylated according to the invention and determining the phosphorylation state of the Apoptin.

In all these examples, Apoptin provided to the cells is preferably non-phosphorylated Apoptin. After incubation with, for example, cell lysates, the phosphorylation state can be detected according to a method described herein. Even more preferably, Apoptin comprises a protein fusion. Protein fusion is well known in the art and can be N-terminal and/or C-terminal linked: examples are histidine fusions or maltose binding protein fusions. An example of an Apoptin protein fusion is His-Vp3 or MBP-Vp3 as described in the detailed description herein.

DETAILED DESCRIPTION OF THE INVENTION

Figure 1:
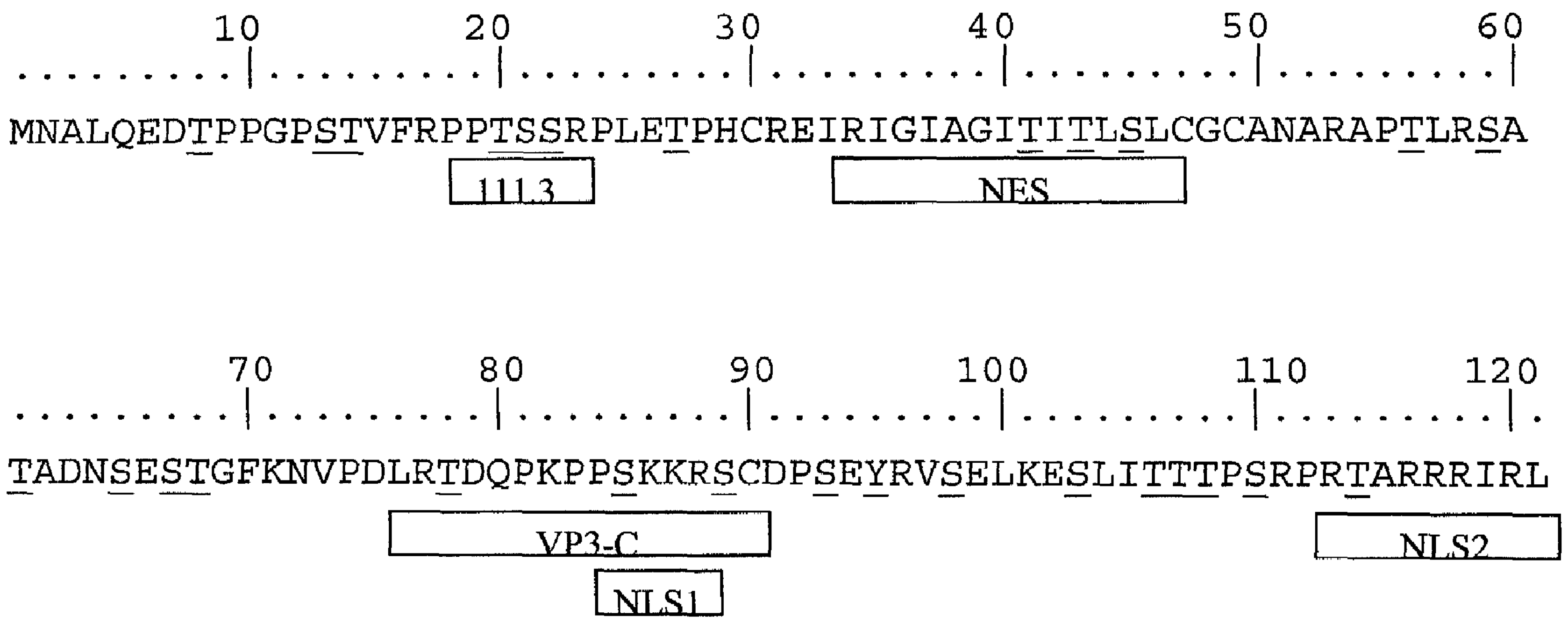
FIG. 1. The complete amino acid sequence (SEQ ID NO:1) of the Apoptin protein that is encoded by pCMV-Vp3 and by the GFP-Apoptin constructs. (Note that the Apoptin protein encoded by the pIRESneo alanine mutants is a natural, phenotypically similar variant containing a K at position 116 (SEQ ID NO:2).) Boxed underneath the primary sequence are various domains of Apoptin: 111.3, the epitope for monoclonal antibody 111.3; NES, the putative nuclear export signal; Vp3-C, corresponds to the peptide used to raise the polyclonal antibody Vp3-C; NLS1 and NLS2, the two putative nuclear localization signals in the potential bipartite arrangement. All potential conventional phosphorylation sites (serines, threonines and the sole tyrosine) are underlined.

In another embodiment, the invention comprises a kit for detecting the presence of cancer cells or cells that are cancer prone or a kit for testing the in vitro treatment effect of Apoptin on tumor cells. Such a kit comprises an antibody according to the invention.

An example of a kit is described in more detail below:

The fact that lysates of tumor or transformed cells are able to phosphorylate Apoptin in vitro forms the basis for a rapid, non-subjective, low-labor-intensive diagnostic kit that is able to determine whether a patient's biopsy is cancerous, or, more importantly for early therapeutic intervention, cancer-prone. An advantage of such a method is that one does not need to culture primary (tumor) cells under tissue-culture conditions, which, in many cases, proves to be difficult or impossible. A kit would be divided into, for example, three components:

1) Patient Biopsy Sample (Provided by a Doctor)

2) Biopsy lysis and phosphorylation tube, to which the sample is added and incubated 3) ELISA-Based System for Rapid Detection of Apoptin Phosphorylation As an example, a more detailed description of the invention:

1) The sample is straightforward; only a very small amount of suspect material is required. In addition, as a control, the doctor should also take some normal cell material from the same patient; for example, a brief, non-invasive, non-painful scraping of the inside of a patient's cheek would provide a rich source of epithelial cells for analysis. Finally, the kit also provides a standardized lysate of transformed cells as a positive control.

2) The sample is added to the provided lysis tube that already contains a combination kinase incubation/lysis solution optimized for phosphorylation of Apoptin. This comprises, in general, a mild detergent, a buffer, physiological salts, protease inhibitors, phosphatase inhibitors, inorganic phosphate, and recombinant Apoptin protein. The sample is simply added to the tube, mixed briefly and then incubated for 15-30 minutes at 30° C. or other amenable temperature. If the sample of the patient is transformed or tumorigenic, the resident kinase phosphorylates the recombinant Apoptin in the tube, just as the positive control standard lysate, but not a negative control lysate derived from the patient's cheek epithelia.

3) ELISA (enzyme-linked immunosorbant assay) is a technique widely used in diagnostic kits (e.g., pregnancy tests, HIV tests) that exploits the ability of a specific antibody to bind to the desired antigen; for detection, the antibody is used in combination with a colorimetric readout such that a color appearance or change indicates a positive result, whereas no appearance or change indicates a negative result. Note that the ELISA assay can be performed in a variety of ways, and below is only one example of how it might be performed. Descriptions and protocols for various ELISA strategies are presented in Harlow and Lane, 1988.

An antibody, according to the invention, specific for a phosphorylated epitope of Apoptin, is used in this kit. The ELISA occurs on a solid substrate (e.g., multiwell plate). Attached to the solid substrate is the phospho-Apoptin-specific antibody. The wells are hydrated with wash solution and treated with blocking solution, then the contents of the lysis tubes (sample(s) and controls) are added to the wells. Presumably, multiple patient samples are batch-assayed in parallel; many diagnostic ELISAs feature convenient modular well strips that can be broken off to the number required. In addition, the kit provides a positive control and a negative control for the ELISA itself (for example, phospho-Apoptin peptide solution, non-phosphorylated Apoptin peptide solution and saline solution). After a brief incubation, allowing any phosphorylated Apoptin generated by the kinase in the patient's biopsy to bind to the specific antibody, the rest of the lysate is washed away thoroughly. In particular, all of the non-phosphorylated Apoptin is removed, which is key for the next step. Now, all the wells receive a droplet of, for example, the anti-Apoptin monoclonal 111.3, which recognizes Apoptin regardless of phosphorylation state. This version of 111.3 is pre-conjugated with, for example, the enzyme alkaline phosphatase, which is able to convert the substrate nitrophenyl phosphate into a bright yellow color detectable by eye as well as by a multiwell spectrophotometer. Other combinations of enzymes and substrates are also available (see, Harlow and Lane, 1988, for details). After incubation, allowing 111.3 to bind to the phosphorylated Apoptin captured by the phospho-specific antibody attached to the solid substrate, the wells are washed again. Finally, the enzyme substrate solution is added, and the color is allowed to develop and the reaction is stopped. A color change indicates the presence of phosphorylated Apoptin, which in turn infers the presence of a tumor/transformed-specific kinase activity in the patient's sample.

Confirmatory Support Protocol:

ELISA can sometimes produce false-positive results. In the case of serious illnesses such as HIV, a positive ELISA result is then grounds for a more precise, labor-intensive assay to confirm the ELISA result. In the case of the standard HIV ELISA, for example, a positive result is then confirmed by Western Blot analysis. Such a confirmatory protocol would also be appropriate for a cancer diagnostic. A Western blot using the phospho-specific Apoptin antibody is very useful as a confirmation and also forms part of the invention. In conjunction, the doctor could also perform more standard pathology tests.

An ELISA as previously described herein, or any other method known by a person skilled in the art with a sufficient level of sensitivity, is, for example, used to screen simple blood samples of patients who would be expected to have some metastasising tumorigenic cells in circulation. Such a test provides an early identification of cancer patients long before tumors become evident by palpation or x-ray.

The diagnostic kit as described above, in addition to clinical applications, is useful as part of a method to identify a mediator of tumor-specific phosphorylation (for example, a kinase). For example, one way to arrive at such a mediator is to enable or inhibit the phosphorylation and uses the kit as a screening tool.

Furthermore, the invention provides a pharmaceutical composition comprising phosphorylated Apoptin, a vector or a gene delivery vehicle according to the invention.

Such a pharmaceutical composition is, in particular, provided for the induction of apoptosis, for example, wherein the apoptosis is p53-independent, for the treatment of a disease where enhanced cell proliferation or decreased cell death is observed, as is, in general, the case when the disease comprises cancer or autoimmune disease. Herewith the invention provides a method for treating an individual carrying a disease where enhanced cell proliferation or decreased cell death is observed comprising treating the individual with a pharmaceutical composition according to the invention.

The invention will be explained in more detail in the following description, which is not limiting to the invention.

EXPERIMENTAL PART

Plasmids

Description of pCMV-Apoptin and pCMVneo

The plasmid pCMV-Apoptin, which encodes a naturally occurring form of Apoptin, was described previously by Danen-Van Oorschot et al. (1997). In short, the plasmid pCMV-Apoptin contains the human cytomegalovirus (CMV) promoter and CAV DNA sequences (nt 427-868) encoding Apoptin exclusively. The synthesized Apoptin protein harbors apoptotic activity and is identical to GenBank Q99152 except position 116 contains a K>R change. The empty vector pCMV-neo was described by Baker et al. (1990) and is used as a negative control. FIG. 1 shows the amino acid sequence of the Apoptin protein with its domains and potential phosphorylation sites indicated.

Construction of N-Terminal Deletion Mutants of Apoptin Fused to GFP

Figure 2:
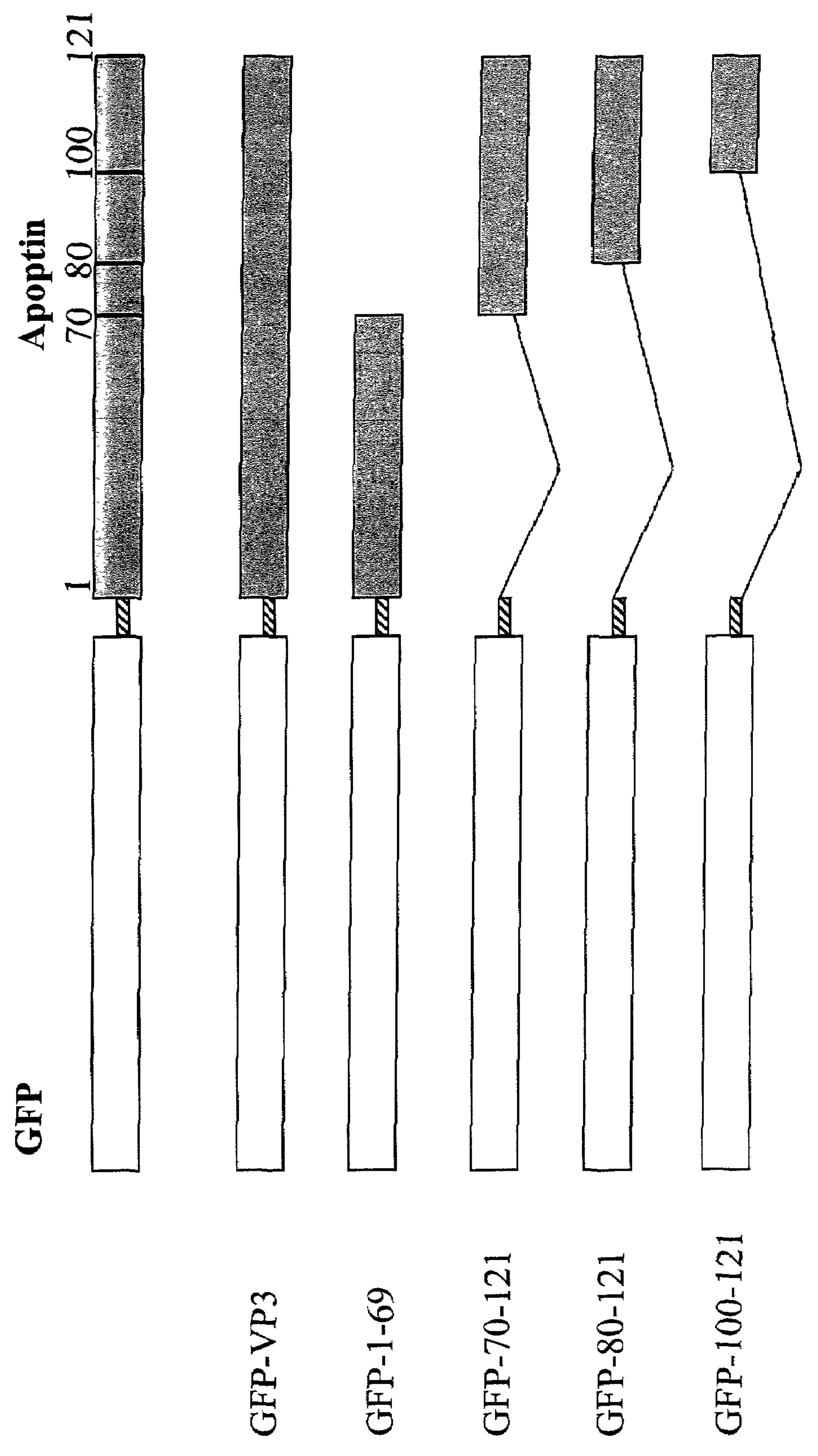
FIG. 2. A schematic representation of the GFP-fused mutant series of Apoptin. The sizes depicted are not to scale. White boxes, the green fluorescence protein (GFP) tag; grey boxes, the Apoptin fragment; black bars show the approximate location of the amino acid numbers on the boundaries of the deletions; striped boxes, a tether region between the GFP and Apoptin fragments; bent lines indicate where the deletion occurs.

N-terminal deletion mutants of Apoptin were fused C-terminally to GFP in the vector phGFPS65T obtained from ClonTech (USA). Briefly, GFP containing an activating mutation is juxtaposed, via a 4 amino acid tether, to full-length Apoptin (GFP-Vp3) or portions thereof: GFP-1-69, GFP-70-121, GFP-80-121 and GFP-100-121, where the numbers indicate the amino acid residues of Apoptin included in the construct. The GFP-Vp3 fusion genes are under the regulation of the SV40 promoter, which is active in a broad range of mammalian cell types. FIG. 2 depicts the GFP mutants in schematic form.

For the construction of pGFP-Vp3, the NdeI-BamH1 fragment of the plasmid pGBT9-Vp3 (Noteborn and Danen-Van Oorschot, 1998) was isolated and cloned in the BsrGI and NotI sites of the linearized phGFPS65T plasmid.

For the construction of pGFP-1-69 and pGFP-70-121, respectively, the NdeI-BamH1 fragment of plasmid pGB9-Vp3 was treated with restriction enzyme BsrI. The BsrGI-BsrI fragment and the required BsrGI-NdeI and BsrI-NotI linkers were cloned in the BsrGI-NotI-treated pGFPS65T plasmid, resulting in the pGFP-1-69 plasmid vector, whereas theBsrGI-BamH1 fragment and the required BamHI-NotI linker were cloned in the BsrGI-NotI-treated pGFPS65T plasmid, resulting in GFP-70-121.

For the construction of GFP-80-121, a PCR DNA fragment encoding the amino acids 80-121 of the Apoptin gene was produced. The phGFPS65T plasmid and the PCR fragment were digested with the restriction enzymes BsrGI and NotI. Subsequently, thecleavedPCR fragment was cloned in the CIP-treated phGFPS65T plasmid.

For the construction of GFP-100-121, aPCR DNA fragment encoding the amino acids 100-121 of the Apoptin gene was produced. The phGFPS65T plasmid and the PCR fragment were digested with the restriction enzymes BsrGI and NotI. Subsequently, the cleaved PCR fragment was cloned in the CIP-treated phGFPS65T plasmid.

Construction of Alanine Mutants

Figure 3:
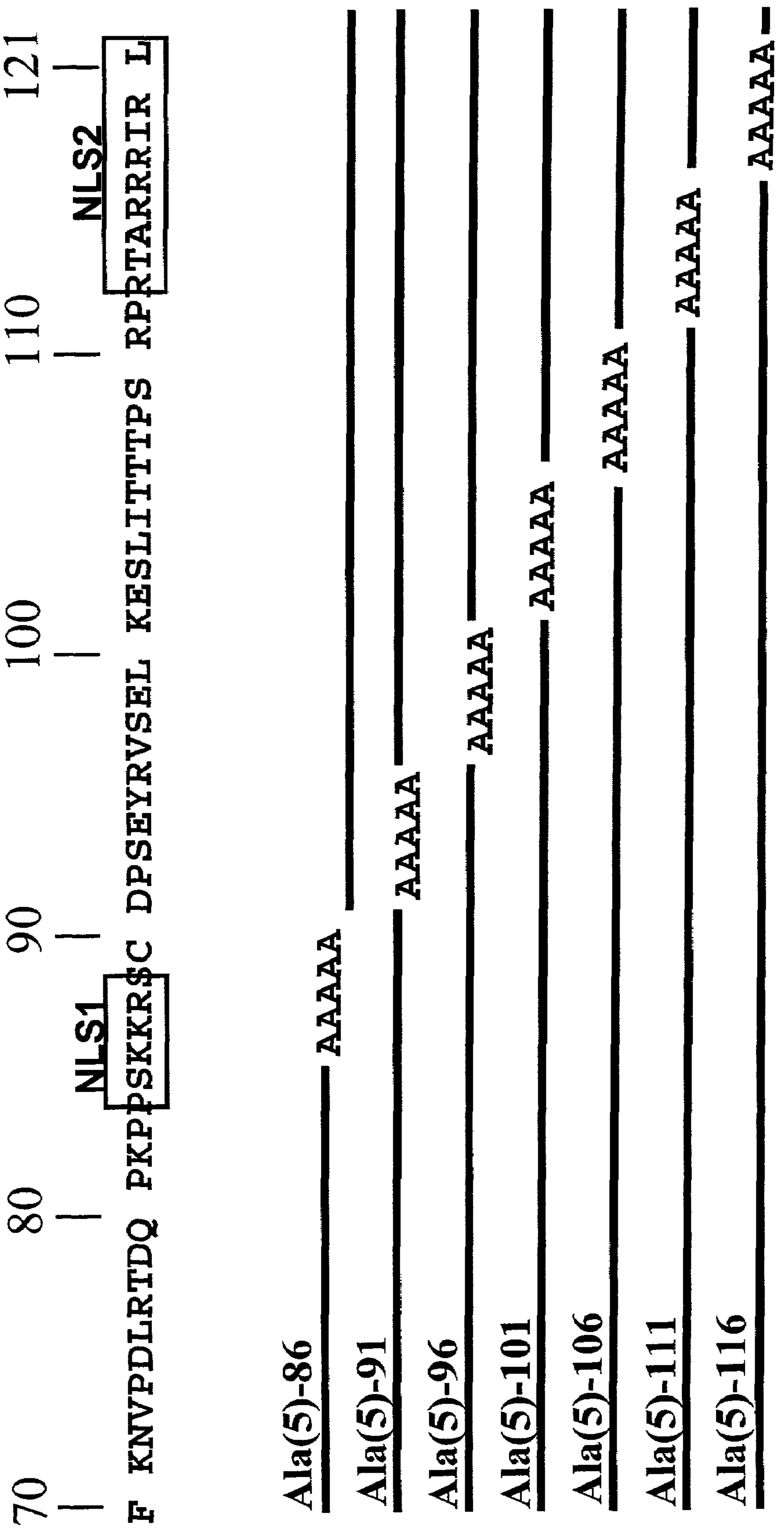
FIG. 3. A schematic representation of the 5-alanine linker-scanning mutant series of Apoptin (SEQ ID NOS:3-9, as labeled). Only the region between 70 and 121 is shown. The amino acid sequence (residues 70-121 of SEQ ID NO:1) is shown on the top, including the NLS domains (boxed) for reference. The entire Apoptin sequence is identical (heavy black lines) except where the alanine replacements are depicted.

A series of 5-Alanine (Ala(5)) scanning mutants of the Apoptin gene was a kind gift from Dr. D. Mumberg from Schering AG, Berlin. First, an Apoptin DNA was constructed containing additional unique restriction enzyme sites that allow for ease of cloning of systematic Ala(5)-mutants. Then, sequential stretches of 5 amino acids of Apoptin were systematically exchanged by 5 Ala residues, each using a linker substitution strategy. The Ala(5)-mutants have been sequenced and cloned in a modified expression plasmid vector pIRESneo (ClonTech, USA) under the control of the CMV promoter. The relevant Ala(5)-mutants of Apoptin are shown in FIG. 3.

Construction of nls-1-69 Apoptin

DNA encoding the SV40-Large T nuclear localization signal (PPKKKRKV) (SEQ ID NO:20) was fused N-terminally to an NdeI/BsrI fragment of Apoptin, derived from the parental Apoptin plasmid pET16b-Vp3, encoding amino acids 1-69 of Apoptin. The resulting plasmid, called pCMV-nls-Vp3(1-69), was confirmed and shown to express a nuclearly localized Apoptin fragment.

Construction of Threonine and Proline Replacement Constructs

Figure 4:
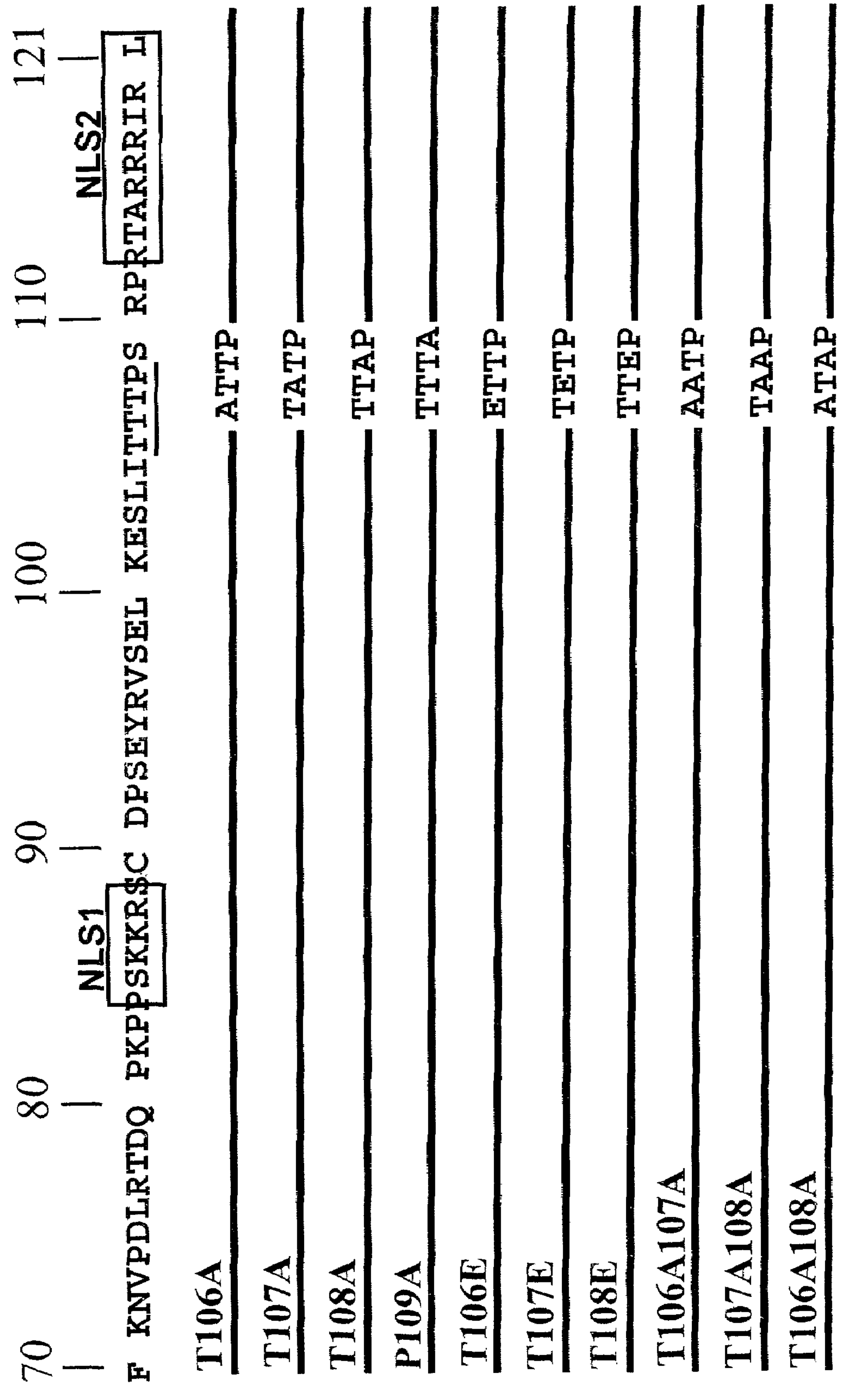
FIG. 4. A schematic representation of the single- and double-point mutant series of Apoptin (SEQ ID NOS: 10-19, as labeled). Only the region between 70 and 121 is shown. The amino acid sequence (residues of 70-121 of SEQ ID NO:1) is shown on the top, including the NLS domains (boxed) for reference. The entire Apoptin sequence is identical (heavy black lines) except where the alanine or glutamic acid replacements are depicted. The mutated region between 106 and 109, inclusive, is underlined on the reference sequence.

Further, we received (a kind gift from Schering AG, Berlin, DE) a number of threonine replacement mutants of Apoptin and one proline replacement mutant, either using alanine to eliminate potential phosphorylation or glutamic acid to mimic constitutive phosphorylation. The strategy used was the same as for the Ala(5)-mutants (see above) except that the linkers contained the appropriate point mutations. These constructs are depicted in FIG. 4.

Cloning of the His-Tagged Vp3 Construct

Vp3 lacking a stop codon was cloned in the NdeI site and NotI site of the IPTG-inducible bacterial expression plasmid pET22b, which provides in frame a 6-histidine tag and a stop codon. The essential regions of the final pVp3H6 DNA construct were confirmed.

All cloning steps were performed essentially according to Maniatis et al. (1982) and sequencing of all constructs was based on the method described by Sanger et al. (1977) at Baseclear, Leiden or at Schering AG, Berlin.

Vp3H6 Expression and Purification

The Vp3H6 construct was transformed in BL21(DE3) bacteria (Novagen) and a colony was grown at 37° C. to an OD600 of ca. 0.6. Expression was then induced by adding 1 mM IPTG and the cells were grown for an additional 3 hrs. After harvesting by centrifugation, the cells were lysed in a Bead-Beater (Biospec Inc.) in lysis buffer (containing 50 mM NaHEPES pH 7.4, 100 mM NaCl, 1 mM EDTA, 1 mM DTT and protein inhibitors (Complete, Boehringer)). The inclusion bodies were harvested by centrifugation and made soluble by suspending in Solubilization Buffer (containing 50 mM HEPES pH 7.4, 20 mM Glycine, 1 mM EDTA, 10 mM DTT, 8 M Urea). The cleared supernatant was loaded directly on UNO-S12 (Biorad) pre-equilibrated with: 20 mM $KPO_4$, 5 mM Imidazole, 6 M urea, 1 mM GSH. The His-tagged Vp3 protein (Vp3H6 protein) was eluted with an NaCl gradient (0-1M NaCl at 3 ml/min with a total volume of 200 ml). Vp3H6 was eluted between 400 and 650 mM NaCl. It was loaded directly on Ni-NTA (Qiagen) (pre-equilibrated in 20 mM $KPO_4$ pH 7.4, 5 mM Imidazole, 500 mM NaCl, 6 M urea at 4° C.). Next, the column was washed with 20 mM $KPO_4$ pH 7.4, 20 mM Imidazole, 500 mM NaCl, 6 M GuHCl. The GuHCl was removed by washing with 20 mM $KPO_4$ pH 7.0, 400 mM NaCl, 2 mM MgCl2, 1 mM GSH, and Vp3H6 protein was eluted with 20 mM $KPO_4$ pH 7.4, 400 mM NaCl, 500 mM Imidazole, 2 mM MgCl2. The Vp3H6 protein containing peak fractions was pooled and 5 mM EDTA was added to remove nickel traces. The sample was dialyzed (1 volume to 200) to 20 mM $KPO_4$ pH 6.5, 400 mM NaCl, 2 mM MgCl2, 1 mM DTT. Finally, the Vp3H6 protein was concentrated on Centricon YM3 filters (Millipore) to at least 7 mg/ml.

Cloning of MBP-Vp3-Based Constructs

The Apoptin gene was fused in frame in a bacterial expression vector encoding the Maltose-binding protein (MBP), a 10 Asn linker and a Thrombin site. The expression system is based on a modified pMal-c2 plasmid vector (New England Biolabs, USA), in which the factor Xa site has been replaced by a thrombin site. This modified vector was named pMal TB. A PCR fragment consisting of the complete Apoptin sequences and at the 5'-end a BamHI site and at the 3'-end a SalI site was cloned in pMal TB. The resulting fusion product consists of an N-terminal MBP moiety that is separated from the Apoptin part by a 10-Asn linker and a thrombin-cleavage site. The resulting plasmid is called pMBP-Vp3 and the proteinaceous substance encoded by this plasmid is designated MBP-Vp3. The correct sequence of the essential parts of the MBP-Vp3 construct was confirmed by means of the Sanger method (Sanger et al., 1973) and carried out by Base-Clear, Leiden, NL.

Using the same cloning and verification strategy, we also prepared an Apoptin gain-of-function expression construct called MBP-Vp3-T107E. The only difference between MBP-Vp3 and MBP-Vp3-T107E is a single replacement mutation encoding a glutamic acid instead of a threonine at position 107.

Purification and Expression of MBP-Vp3-Based Proteins

The Plasmids pMBP-Vp3 and MBP-Vp3-T107E were transformed into bacteria derived from strain BL21(DE3), and initial expression studies showed that the resultant proteins constituted roughly 10% of the soluble cytoplasmatic protein after 3 hours induction with 1 mM IPTG. Purification was carried out on amylase beads at pH 7.4 and 1M NaCl. Subsequently, elution in buffer containing 20 mM HEPES pH 8.0, 50 mM NaCl, 1 mM EDTA, imM DTT, 10 mM maltose, yielded about 100 mg protein per liter of bacterial culture. This purified protein was loaded on a UNO-S 1 chromatography column (Biorad), and the fractions that elute at 400-500 mM NaCl, 20 mM HEPES pH 7.4, 1 mM EDTA were pooled, dialyzed against PBS and concentrated with Millipore UltraFree spin filters.

The negative control preparation, Maltose binding protein (MBP), was produced and purified in the way described for MBP-Vp3.

Cloning of GST-Vp3 Construct

Apoptin was cloned (at Schering AG Berlin), using unique BamHI and EcoRI restriction sites, into the bacterial expression vector pGEX-T vector and was verified by restriction analysis and sequencing. The resulting construct was called pGEX-T-GST-Vp3.

Expression and Purification of GST-Vp3 Recombinant Protein in *E. Coli* pGEX-T-GST-Vp3 was transformed into *E. coli* BL21-RIL (Stratagene), and the resulting strain of pGEX-2T-Apoptin BL21-RIL (9 Liter of culture) was fermented according to standard procedures. Cells were harvested and suspended in 20 mM Tris-HCl pH 8, 5 mM DTT, 0.1 mM PMSF. Next, disruption buffer (20 mM Tris pH 8, 1.6 M NaCl, 5 mM DTT, 5 mM EDTA, 3 M Urea) and 0.1 mM PMSF were added, and disruption was achieved in a MiniLab 40 Homogenizator, 2 times at 700 bar. After centrifugation at 40,000, the supernatant was bound to Glutathione Sepharose (Pharmacia) overnight at 4° C. Next, the Glutathione Sepharose washed on a glass funnel G3 with disruption buffer+1.5M urea and loaded into an XK 26/20 column. Chromatography was performed ($ÄKTA_{FPLC}$, Software UNICORN 3.21), washed with disruption buffer+1.5M urea, followed by a wash with disruption buffer without urea. The protein was eluted with disruption buffer lacking urea but containing 15 mM reduced Glutathione, and the fractions were analyzed by SDS-PAGE.

Positive fractions were pooled, glutathione was removed, and the final protein was concentrated by ultra filtration (Centriprep 30). Aliquots were stored at 80° C.

Cell Lines and Culturing

The following established cell lines have been described previously: Saos-2 human osteosarcoma cells (Diller et al., 1990), which are functionally deficient for p53 function; U2OS human osteosarcoma cells (Diller et al., 1990), which are functionally competent for p53 function; VHSV (Danen-Van Oorschot et al., 1997) are SV40-large-T transformed VH10 human fibroblasts, SVK14 (Danen-Van Oorschot et al., 1997) are SV40-large-T-transformed keratinocytes, H1299 (Friedlander et al., 1996) are human lung carcinoma cells; primary passage 2 human breast keratinocytes Were a gift from Dr. M. Ponec, Department of Dermatology, Leiden University Medical Center; low-passage primary human fibroblasts (VH10) were a gift from Dr. L. Mullenders, Leiden University Medical Center, Department of Chemical Mutagenesis and Radiation Genetics; 293T cells, which are human kidney cells transformed with adenovirus 5 DNA and with SV40 large T antigen, were a kind gift from Dr. Jean Rommelaere, DFKZ Center in Heidelberg, Germany; the Jurkat human acute T cell lymphoma cell line was a kind gift from Dr. J. P. Medema, Leiden University Medical Center; COS-7 cells, which are SV40-transformed African green monkey kidney fibroblasts, were a kind gift from Dr. A. G. Jochemsen, Leiden University Medical Center; HT29, a human colon carcinoma cell line, was obtained from the European Cell Culture Collection; primary normal low-passage synoviocytes derived from patients with bone fractures were a kind gift from Dr. T. Huizing a, Leiden University Medical Center; LCL, an EBV-transformed B cell line, was a kind gift from Nicola Annels, Leiden University Medical Center; MDCC-MSB1 are Marek's disease-transformed chicken lymphoblastoid cells, as described in Yuasa, N., (1983); MDCC-MSB-1/CAV are MDCC-MSB 1 cells transfected with chicken anaemia virus as described in Noteborn et al. (Gene 233 (1998)); low passage CD31-negative normal diploid skin fibroblasts were a kind gift from Schering AG in Berlin; human mesenchymal stem cells were purchased from BioWhitacker (USA).

All cells were cultured in Dulbecco's Modified Eagle Medium supplemented with 10% fetal bovine serum and penicillin/streptomycin, and cultured at 10% $CO_2$ in a humidified 37° C. incubator, except for the primary keratinocytes, which were grown in DMEM/Hams F12 (3:1), supplemented with 5% bovine calf serum (Hyclone), 10-6 M isoproleronol, 10-6 M hydrocortisone, 10-7 M insulin, and penicillin/streptomycin and cultured at 37° C. at 7.5% $CO_2$. The mesenchymal stem cells were cultured in dedicated medium purchased from the manufacturer for no more than 4 passages, using their protocols.

Primary Tumor Tissue

Primary human tumor samples were a kind gift of Schering AG in Berlin. During routine surgical procedures to remove malignant material from one human patient with esophageal cancer and one patient with colon carcinoma, a portion of the tumor mass (approximately 1 cc) was set aside, shock-frozen in liquid nitrogen, shipped to our laboratory on dry ice and stored at −70° C. until further use.

Transfections and Microinjections

For biochemical analyses, cells were plated the day before on 10 cm dishes such that cultures were 40% confluent at the time of transfection. Seven μg DNA was transfected using a 3:1 (μl:μg DNA) ratio of FuGene 6 (Roche) according to the manufacturer's instructions. The complexes were incubated on the cells in the presence of full serum and were left on until the cells were assayed. For apoptosis immunofluorescence assays, $0.5\times10^5$–$1\times10^5$ cells were plated on 2-well PERMANOXT chamber slides (Nunc) and transfected the same as for 10 cm plates, except that only 1.5 μg DNA per well was used and the rest of the transfection components were scaled down accordingly. When microinjections were used instead of transfections, the following procedures were followed. Cells were cultured on glass-bottomed microinjection dishes. The cells were micro-injected in the cytoplasm with protein at 3 mg/ml using an Eppendorf microinjector with the injection-pressure condition of 0.5 psi or in the nucleus in the case of DNA (100 mg/μl). The cells were co-injected with Dextran-Rhodamine (MW: 70 kda; Molecular Probes, Leiden, NL) to be able to later identify injected cells. The cells were incubated at 37° C. after injection until the cells were fixed with formaldehyde-methanol-acetone and stained and analyzed as described in the section "apoptosis assays" using Vp3-C as a primary antibody.

In Vivo Orthophosphate Metabolic Labeling Assay

Forty-eight hours post-transfection, cultures transfected with Plasmids encoding Apoptin, mutant Apoptin, or controls were washed two times with phosphate-free DMEM (PFD; Sigma), then incubated for ten minutes in PFD in the tissue culture incubator to deplete intracellular phosphate. Next, the plates were incubated with PFD supplemented with $^{32}$P-orthophosphate (0.5-1.25 mCi/ml) for four hours. Cells were washed with ice-cold PBS, then lysed in 1 ml RIPA buffer (10 mM Tris pH 7.5, 150 mM NaCl, 0.1% SDS, 1% NP-40, 1% sodium deoxycholate, supplemented with the following protease or phosphatase inhibitors at standard concentrations: trypsin inhibitor, pepstatin, leupeptin, aprotinin, PMSF, bb-glycerophosphate, sodium vanadate, and sodium fluoride). Lysates were incubated on ice for 30 minutes and centrifuged for 10 minutes at 13,000 rpm in a refrigerated microfuge, and the supernatants were immunoprecipitated with affinity-purified polyclonal rabbit serum (Vp3-C) raised against the C terminal portion of Apoptin and protein A beads using standard methodology. The final pellet was resuspended in 2× denaturing Laemmli buffer and stored at −20° C. until processing.

Immunoprecipitation samples were divided into two aliquots, one consisting of 2 mml and the other of the remainder (38 mml). Each set was run on parallel 15% SDS-PAGE gels; the 38 mml gel sets were dried, whereas the 2 mml gel sets were Western-transferred to Immobilon membranes (see below). The dried gels containing the bulk of the immunoprecipitates were subjected to autoradiography to visualize phosphorylated protein, whereas the parallel membranes were immunoprobed to confirm the presence of Apoptin in the lysates, regardless of the phosphorylation state. In some cases, the 38 mml gels were not fixed but the entire experiment was transferred to Immobilin via Western blotting, autoradiography was performed on the Immobilin and then the membrane was Western-immunoprobed for precise overlaying of the radioactive signal with the Western signal. All autoradiographs were exposed along with fluorescent marks to facilitate subsequent orientation for band isolation (see below).

Western Blot Analysis

Protein was electroblotted from gel to PVDF membranes (Immobilin, Millipore) using standard techniques. Membranes were blocked in a tris-buffered saline solution supplemented in 0.5% Tween-20 (TBS-T) and 5% non-fat dry milk (TBS-TM) for 30 minutes, washed briefly in TBS-T, then incubated for 1 hr at room temperature with primary antibody, depending on the experiment, in TBS-TM at the following concentrations: 111.3 hybridoma supernatant (monoclonal recognizing the N-terminus of Apoptin) at 1:25; Vp3-C purified serum at 1:3; or anti-GFP (Living Colors Peptide Antibody, Clontech) under conditions recommended by the manufacturer. After 3×5' washes in TBS-T, membranes were further incubated in the appropriate antibody (anti-mouse Ig, anti-rabbit Ig,) or Protein A (for GFP mutants of a size that co-migrates with contaminating heavy-chain immunoglobulin) conjugated to horseradish peroxidase (HRP). After 3×20' washes in TBS-T, membranes were subjected to enhanced chemiluminescence using standard techniques, exposed to x-ray film (Kodak), and films were developed using standard automated methods.

When using the phosphospecific Apoptin antibody for Western blot analysis, everything was as described as above for Vp3-C with the following exceptions: after being blocked in TBS-TM, the filters were washed 3×20' each in TBS-T to remove all traces of soluble milk, and subsequent to that, for every step requiring TBS-TM, a BSA-based solution was substituted (TBS-TB: TBS-T+3% bovine serum albumin). The purified antibody was used at a dilution of 1:1000 (approximately 1 μg/ml final).

Phosphoamino Acid Analysis (PAA)

Using exposed autoradiography films for orientation, bands visualized in the ortholabelling experiments (above) corresponding to phosphorylated Apoptin (P-Apoptin) or the corresponding region in negative control lanes were excised from the PVDF membranes using a razor blade. Membrane fragments were rehydrated with methanol, blocked in 0.5% polyvinylpyrrolidone-360,000 in 100 mM acetic acid for 30' at 37° C., washed 5× with water and 2× with 0.05 M $NH_4HCO_3$ trypsin buffer, then digested overnight with 10 μg trypsin (Tpck-treated, Worthington, USA) in trypsin buffer at 37° C. to remove all proteins from the membrane. Samples were digested a second time for two hours, and the supernatant was supplemented with water and split into two samples, one for PAA and one for tryptic phosphopeptide analysis (see below). PAA samples were further processed using the method of Hunter (basically as described in the text of "Protein phosphorylation. Part B: Analysis of protein phosphorylation, protein kinase inhibitors, and protein phosphatases", *Methods Enzymol.* 1991, 201). Briefly, the peptides were lyophilized, hydrolyzed for 1 hr in 6N HCl at 110° C., lyophilized, then resuspended in pH 1.9 buffer, supplemented with non-radioactive PAA standards (1.0 mg/ml of each P-Thr, P-Ser, and P-Tyr, Sigma) and spotted onto precoated cellulose TLC plates (Merck). On a Hunter thin-layer electrophoresis apparatus, plates were run in the first dimension at 1.5 kV for 20' in pH 1.9 buffer, dried, turned 90 degrees counterclockwise and run again in the second dimension at 1.3 kV for 16' in pH 3.5 buffer. After drying the plate, PAA standards were visualized by spraying with 0.25% ninhydrin in acetone and baking the plates at 65° C. for 10' to develop the color. Finally, plates were exposed to PhosphoImage screens to detect the radioactive phosphoamino acids.

Tryptic Phosphopeptide Mapping (TPM)

Samples split off from the PAA procedure (see above) were subjected in parallel to TPM analysis using the method of Hunter (for reference see above). Briefly, samples were lyophilized, oxidized for 1 hr on ice in freshly-prepared performic acid, supplemented with water and lyophilized again. Samples were resuspended in pH 1.9 buffer and loaded onto TLC plates. On a Hunter thin-layer electrophoresis apparatus, plates were run in the first dimension at 1 kV for 25' in pH 1.9 buffer, dried, then placed in the same orientation in a liquid chromatography tank with Phospho-Chromo buffer overnight for the second dimension (no more than 15 hours). Plates were then dried and exposed to PhosphoImage screens to detect the radioactive phosphopeptides. Predicted trypsin cleavages were determined by the ExPASY computer program Peptide Mass.

In Vitro Phosphorylation of Recombinant Apoptin

Soluble, purified, recombinant Apoptin protein fused N-terminally to a histidine tag (His-Vp3) and fused N-terminally to maltose binding protein (MBP-Vp3) and produced in *E. coli* bacteria were a gift from RutgerLeliveld, Department of Chemistry, Leiden University (for cloning, production and purification see above). Proteins can only be produced in *E. coli* in an unphosphorylated state, so the His-Apoptin and MBP-Apoptin serve as a good substrate to test whether tumor lysates are able to phosphorylate Apoptin.

Cell types tested included Saos-2, U2OS, Jurkat, Cos, synoviocytes from bone fracture patients, LCL, MSB-1, CD31-, VH10, mesenchymal stem cells, and keratinocytes. All cultured cells to be tested were washed twice with ice-cold PBS, scraped on 0.5 ml ice cold PBS with a rubber policeman, transferred to Eppendorf tubes and centrifuged two minutes at 4000 rpm in a cold microfuge. (Cell pellets can be snap-frozen in liquid nitrogen and stored at −70° C. if not used immediately, with no adverse effect.) Supernatants were removed, and 50-100 μl of kinase buffer (20 mM Hepes pH 7.2, 10 mM MgCl2, 10 mM KCl, 0.5 mM trypsin inhibitor and 0.1 mg/ml $Na_3VO_4$) was added. Samples were frozen-thawed three times, alternating between ethanol/dry ice and regular ice to lyse the cells, then were centrifuged at 14,000 rpm in the microfuge. The supernatants were transferred to fresh tubes as the final cellular lysates.

For primary human tumor samples (colon and esophageal), supernatant was prepared in the following manner. While still frozen, a tiny slice (approximately one cubic millimeter) of the main mass was quickly excised with a scalpel and pulverized through a nylon mesh cell strainer (100 μm, BectonDickenson) in a small volume of kinase buffer, in a small plastic dish on ice. This straining was followed by 2-3 washes (total volume, approximately 200 μl) to maximize yield. The dissociated cells were then pooled in Eppendorf tubes and snap-frozen and stored at −70° C. until further use. When thawed, these samples were treated as the first thaw of the 3×-freeze-thaw cycle and processed in parallel from that point onward with the other cell line supernatant samples.

Protein concentration was determined at OD595 using the Biorad Bradford reagent according to standard procedures. Equal amounts of cellular lysate supernatants (3-60 μg) were incubated for 30' at 30° C. with 0.5 mg of the recombinant Apoptin protein, 50 μM ATP, 0.5 μCi of γ-$^{32}$P-ATP, 1 mM DTT and kinase buffer to bring the total volume to 30 μl. Samples were run on SDS-PAGE gels (same procedure as described in "Western blot analysis"), which were fixed and then visualized by autoradiography. Parallel non-radioactive reactions were carried out and treated identically, except that the resultant gels were subjected to Western blot analysis with the antibody 111.3 (same as within in vivo section) to confirm the presence of the Apoptin protein.

In some cases, a non-radioactive alternative to the in vitro kinase assay was performed. For this procedure, everything was done the same except that at the point of the reaction, an equal concentration of non-radioactive ATP was substituted for the radioactive isotope. Analysis was performed on Western blotted samples using a phosphospecific Apoptin antibody (see "Western blot analysis", above).

In some cases, a slightly different kinase buffer or procedure was used with successful results. For example, we also achieved robust in vitro phosphorylation by preparing cell lysates in a basal kinase buffer composed of 20 mM Tris pH 7.6, 300 mM NaCl, 30 mM $MgCl_2$, and 3 mM $MnCl_2$.

In the case of MBP-Vp3-based assays, the assay could be made even more sensitive and clean by including a purification step prior to SDS-PAGE. In this case, following the reaction, the protein substrate was purified in RIPA buffer either by standard immunoprecipitation (same procedure as described above for the in vivo labelling assay) with protein-A agarose beads coupled to Vp3-C, a polyclonal antibody recognizing Apoptin, or by amylose beads, which are specific for the MBP fusion component. Beads were washed three times prior to the final samples being loaded on SDS-PAGE gels.

Mass Spectrometric Analysis of In Vitro-Phosphorylated Apoptin

To confirm the precise in vitro phosphorylation site of Apoptin in Saos-2 cells, in vitro phosphorylated GST-Vp3 protein (radioactive method, see above) was purified from the lysates by standard glutathione sepharose purification. This material was subjected to carboxymethylation, precipitated with trichloroacetic acid, and, following resuspension, was digested with Tpck-treated trypsin. The peptides were eluted and the radioactive fractions identified using reverse-phase high performance liquid chromatography (RP-HPLC). The fractions containing radiolabelled phosphate additions were then subjected to matrix-assisted laser desorption/ionization (MALDI) analysis on a Voyager-DE STR (Applied Biosystems). Phosphorylated peptides were analyzed by electrospray ionization collision-induced dissociation (ESI-CID) on a QSTAR (Applied Biosystems) to assign the phosphorylated modification to a particular amino acid residue. All mass spectrometric procedures and analyses were standard and were performed at or subcontracted by Schering AG, Berlin.

Apoptosis Assays

Constructs encoding Apoptin or mutants thereof, or lacZ-myc plasmid (pcDNA3.1/Myc-His LacZ, Invitrogen) as a negative control, were transfected into cells in chamber slides, and apoptosis was scored 3-5 days later as previously described (Danen-Van Oorschot et al., 1997). Briefly, cells were fixed with 80% acetone, immunostained using 111.3 as a primary antibody for Apoptin (mutants), or 9E10 anti-myc monoclonal (Evan et al., 1985) for the lacZ-myc control, using FITC-conjugated goat-anti-mouse Ig as a secondary antibody, and counterstained with DAPI. Slides were coded by an individual not performing the scoring, mounted in DABCO/glycerol with coverslips and inspected by fluorescence microscopy. Only positive cells were assessed for apoptosis using nuclear morphology as the criterion. At least 100 cells per well were scored and the assays were done multiple times.

Generation and Use of a Phosphospecific Antibody for Apoptin

Phosphorylation of a protein often creates anew immunological epitope (Blaydes et al., 2000). In order to generate polyclonal antisera specific for phosphorylated Apoptin (i.e., Apoptin in a transformed or tumor environment), we designed the following peptides: SLITTTPSRPRTA (corresponding to residues 103-115 of SEQ ID NO:1) with either the first, the second or the third threonine phosphorylated (residue 106, 107 or 108). These peptides were synthesized at Eurogentec (Belgium) and all subsequent antibody syntheses, purification and preliminary testing were also performed there. In short, these peptides were coupled to Keyhole Limpet Hemocyanin (KLH) and injected as a cocktail into two separate specific pathogen-free rabbits with an immunization schedule of one injection and three subsequent boosts. Blood samples were taken before and after immunization. The titers from all rabbits were high (>200,000). The sera were tested for specific reactivity to the appropriate phosphorylated peptide by ELISA. In order to separate from the total antibody population in serum the antibodies reacting specifically to the phosphate epitope (hereafter also to be referred to as "phosphospecific antibodies" or "PSA") from antibodies reacting to amino acids in common to both phosphorylated and unphosphorylated forms (hereafter also to be referred to as "non-phosphospecific antibodies" or "NPSA"), Eurogentec performed double purification. First, the serum was purified against the phosphorylated peptide. Those recovered antibodies were then passed over a non-phosphopeptide column. The flow-through was designated PSA and what bound was recovered and designated NPSA. PSAs were confirmed by competitive ELISA tests using pre-incubations with various phosphorylated or non-phosphorylated peptides as appropriate, with promising indications, and the antibodies were then shipped to our laboratory. The next nomenclature for these antibodies is also used: 106-X, 107-X and 108-X are the non-phosphospecific antibodies (NPSA); 106-P, 107-P and 108-P are the phosphospecific antibodies (PSA).

We further tested the candidate PSAs and NPSAs by Western blot. For tumor samples, we used lysates of Saos-2 cells transfected with CMV-Vp3, known by in vivo phosphorylation assays to harbor the phosphorylated form of Apoptin. For non-tumor samples, we used both MBP-Vp3 recombinant protein, which cannot be phosphorylated by *E. coli*, or lysates of normal VH10 fibroblast cells transfected with CMV-Vp3, which are known from the in vivo assay to harbor Apoptin that is not phosphorylated. Samples were subjected to Western blot analysis, as described above, and probed in parallel with the PSAs, the NPSAs, and as a control for total Apoptin, the monoclonal antibody 111.3 which recognizes Apoptin regardless of its phosphorylation state. We also tested the utility of the PSAs and NPSAs in immunofluorescence analysis of Saos-2 tumor cells or CD31- normal fibroblasts grown on glass cover slips and expressing transduced CMV-Apoptin DNA. These assays were performed just as for the apoptosis assay (above) except that the PSA or NPSA was incubated at a concentration of 1:100 in conjunction with the antibody 111.3, and each primary antibody was labelled with a differently conjugated secondary antibody (FITC or rhodamine) so that both phosphorylated and non-phosphorylated Apoptin could be visualized in the same cell.

ELISA Test (ApoCheck™) for Tumor or Other Relevant Aberrant Cell Diagnostics

All ELISA methodology was performed using standard procedures known in the art. Briefly, 96-well ELISA plates were coated with phosphospecific antibodies 106-P, 107-P or 108-P, then blocked with bovine serum albumin. Next, the serially diluted test samples, which consisted, for example, of either recombinant MBP or MPB-Vp3 protein reacted with Saos-2 tumor cell lysates of CD31- normal fibroblast lysates in a non-radioactive in vitro kinase assay (see in vitro kinase assay section), were incubated in the wells. After washing, purified 111.3 anti-Apoptin antibody was incubated in the wells. After washing, horseradish peroxidase-conjugated goat-anti-mouse Ig was incubated in the wells. Finally, for detection, tetramethyl benzidine (TMB) substrate was added for a short incubation, the reaction stopped with hydrogen sulfide, and the absorbance read on a standard plate reader at 450 nm.

Negative controls for this assay included performing a mock reaction, including EDTA to inactivate any kinase, then adding fresh MPB-Vp3 to the "killed" reaction. Also mock reactions were performed on MBP-Vp3 with no lysate added, only the buffer in which the lysates were prepared. All negative controls were successfully negative. In some assays as an additional control, we used the appropriate phosphorylated peptide to compete away the specific signal. This was achieved by pre-incubating the lysate with a 200-fold molar excess of peptide. Finally, as a confirmation control, all reactions were split in half, with one-half undergoing the ApoCheck ELISA and the other half being subjected to Western blot analysis with the appropriate phosphospecific antibody. There was a perfect agreement between the outcome of the ELISA and the outcome of the parallel Western blot.

Gain-of-Function Assay in Normal Cells

Assay was performedjust as for apoptosis assay except that normal cells (VH10, CD31- and mesenchymal stem cells) were transduced with the appropriate glutamic acid mutants of Apoptin (T106E, T107E or T108E), with wild-type Apoptin and LacZ-myc DNA as a control (as described in the section "Transfection and Microinjections"). In addition, we performed further gain-of-function assays after microinjecting MBP-Vp3 or a representative Apoptin containing a negatively charged amino acid in the Triple-T locus (MPB-Vp3-T107E) into the cytoplasm of normal cells.

Results

1. In Vivo Tumor-Specific Phosphorylation of Apoptin

In order to determine whether a phosphorylation event is responsible for the tumor-specificity of Apoptin-induced apoptosis, we first investigated Apoptin expressed in tumor (Saos-2) and normal (VH10) cells, which have been extensively characterized with regards to Apoptin localization and killing in previous reports (reviewed by Noteborn, 1999). The cultures were transfected with pCMV-Apoptin or the empty vector plasmid (pCMVneo), labelled in vivo with $^{32}$P-orthophosphate, immunoprecipitated with anti-Apoptin Vp3-C polyclonal antisera, and then the proteins were resolved by SDS-PAGE. After autoradiography, an approximately 16 kD phosphoprotein of a size consistent with Apoptin was detected in Saos-2 cells transfected with pCMV-Apoptin, but was absent in Saos-2 cells transfected with an empty vector. However, the phosphoprotein was not detected in non-tumorigenic VH10 cells transfected with pCMV-Vp3. In a parallel Western blot analysis using the 111.3 anti-Apoptin monoclonal antibody, we confirmed that Apoptin is strongly detected in all cells in which pCMV-Apoptin was transfected, including the VH10 cells, and that the radioactive phosphorylated bands from tumor cells corresponded in size to the band detected by 111.3.

These results indicate that Apotin is phosphorylated in tumor Saos-2 cells but not in normal VH10 cells.

In order to confirm that this tumor-specific phosphorylation was not merely due to the cell-type difference between osteosarcoma cells and fibroblasts, the ortholabelling assay was repeated with several other cell types. It has been shown previously that VH10 cells, when transiently or stably transformed with SV40 large T antigen (LT), become concomitantly sensitive to Apoptin-induced apoptosis (Noteborn et al., 1998b). The same is true for primary keratinocytes. Thus, we first investigated whether this transformation state correlated with the phosphorylation state of Apoptin, by comparing VH10- and passage 2 keratinocyte-expressed Apoptin to Apoptin expressed in corresponding SV40 LT transformed cell lines VHSV and SVK14, respectively. Only the transformed cells exhibited phosphorylated Apoptin, despite the fact that Apoptin was robustly immunoprecipitated from all cells that were transfected with pCMV-Vp3, as assessed by Western blot analysis. Similarly, Apoptin was also shown to be phosphorylated in U2OS osteosarcoma cells and in H1299 human lung carcinoma.

In conclusion, we have shown that Apoptin phosphorylation, in common with its ability to translocate to the nucleus and induce p53-independent apoptosis, is dependent on the transformed or tumorigenic state of the cell.

2. Tumor Lysates But not Normal Lysates can Phosphorylate Recombinant Apoptin In Vitro To confirm our in vivo results on tumor-specific phosphorylation of Apoptin, we performed an in vitro kinase assay in the presence of $\gamma$-$^{32}$P-ATP using mild cellular lysates from tumor cells or normal cells as a kinase donor, and recombinant, bacterially produced Apoptin as a substrate. This experiment showed that whereas Saos-2 lysates were able to phosphorylate recombinant Apoptin in vitro, lysates from normal VH10 cells could not.

On a very long autoradiographic exposure, an extremely faint phosphorylation signal could sometimes be detected on recombinant Apoptin substrate reacted with normal cell lysates. We estimated by standard phosphorimage analysis that this faint normal cell kinase activity was at least 50-200 times less active than in tumor cell samples. Therefore, we strongly believe that the level is not significant enough to pose a problem either for diagnostics or therapeutics.

We varied the buffer conditions of the in vitro kinase assay and determined that the Apoptin kinase is a fairly stable, robust activity that functions in a variety of buffers; indeed, the kinase could be frozen and thawed repeated and vigorously without undue loss of activity. Interestingly, the presence of various general phosphatase inhibitors, such as sodium fluoride, beta-glycerophosphate, okadaid acid and other inhibitors did not liberate a detectable phosphorylation activity in normal cells. These data are strongly supportive of the model that transformed and tumor cells contain a specific kinase activity, as opposed to both tumor and normal cells having the kinase activity, but normal cells having an additional normal-specific phosphatase activity.

To extend these initial observations and determine how universal the tumor-specific kinase activity was, we repeated these in vitro experiments with other cell types and showed that the correlation of Apoptin phosphorylation with aberrancy held true for all cases tested. Specifically, Apoptin became phosphorylated by lysates prepared from the tumor cell lines representing a variety of cell types and species: U2OS (human osteosarcoma), Jurkat (human T cell lymphoma), COS (SV40-transformed green monkey kidney cells), HT29 (human colon carcinoma cells), LCL (human Epstein-Barr-transformed B cell lymphoma cells) and MCB-1 (Marek's disease-virus transformed chicken T cells). Also supporting the hypothesis that the Apoptin kinase activity in transformed or tumor cell lines is actually found in real human tumor tissue, Apoptin became phosphorylated by lysates prepared from two types of tumor tissue (human colon carcinoma and esophageal cancer freshly isolated from a therapeutic surgical excision). In contrast, Apoptin kinase activity was not found in the lysates prepared from a number of primary, human normal cells: CD31- negative skin fibroblasts, mesenchymal stem cells, joint synoviocytes, or enriched keratinocytes derived from several normal breast tissue samples.

Taken together with the in vivo data reported above, these results strongly support the idea that Apoptin kinase activity, just as Apoptin's ability to enter the nucleus and induce apoptosis, is a general phenomenon associated with the aberrant nature of the cell. Kinase activity that phosphorylates Apoptin represents a key mediator of human cancer, the intervention of which will inhibit tumor growth or survival and diagnosis of which will allow more timely treatment.

In summary, these data are consistent with the in vivo results and also suggest that the tumor-specific phosphorylation seen in vivo was the result of a tumor-specific kinase.

3. Apoptin is Phosphorylated in a Tumor-Specific Manner on Threonine(S)

In order to determine whether tumor-specific phosphorylation of Apoptin is necessary and sufficient for apoptotic activity, we first had to map the relevant site(s). Although Apoptin is a small protein, it contains a large number of potential phosphorylation sites (12 serines, 14 threonines, and one tyrosine, or roughly one-quarter of the protein). A schematic drawing showing the potential phosphorylation sites is depicted in FIG. 1. To narrow down the possibilities, Saos-2 cells were transfected with pCMV-Apoptin or pCMVneo (negative control) and a phosphoamino acid analysis was performed on phosphorylated Apoptin (P-Apoptin) derived from Saos-2 cells to determine whether the modification occurs on threonine, serine or tyrosine residues. We determined that phosphorylation occurs specifically on threonine residues. There was also a fainter phosphoserine signal evident, but as this was also evident in samples corresponding to Saos-2 cells transfected with empty vector and, indeed, in irrelevant cells (e.g., mock-transfected VH10 cells), we conclude that this phosphoserine signal was probably derived from a co-migrating cellular phosphoprotein contaminant, and thus was not significant. However, at this point, the presence of a minor, specific phosphoserine signal could not be ruled out. This result was reproduced in a second tumor cell line (U2OS). In all performed experiments, no indication was found for a phosphorylation event on the tyrosine amino acid.

These data suggest that Apoptin is tumor-specifically phosphorylated on one or more of the 14 threonine residues. However, the presence of a minor, specific phosphoserine signal cannot be ruled out without further experiments, as performed below.

4. Phosphorylation of Apoptin Occurs Between Residues 100-121

In order to narrow down further the region on Apoptin where the phosphorylation occurs, we assayed a series of gross N-terminal deletion mutants of GFP-Apoptin (depicted in FIG. 2). U2OS cells were transfected with the N-terminal deletion mutants of GFP-Apoptin and an in vivo labeling assay (as described before) was performed. GFP alone exhibited a very faint background phosphorylation in this assay, but in contrast, full-length Apoptin fused to GFP was strongly phosphorylated. GFP-1-69, which encodes the N-terminal half of Apoptin, showed only background phosphorylation. In contrast, all the C-terminal fragments were specifically phosphorylated (GFP-70-121, -80-121, and -100-121) in vivo. GFP-100-121 was somewhat less phosphorylated than the others, but still significantly so. Nevertheless, there are no threonine differences between residues 80-100, so the result using the 80-121 mutant should be functionally equivalent in the assay.

In conclusion, a tumor-specific phosphorylation site or sites are likely to reside downstream of residue 100, in a region that contains only four threonines: a triple-T stretch at positions 106-108, and a single T at position 114.

5. Only One Major Tryptic Fragment of Apoptin is Phosphorylated In Vivo

An inspection of the computer-predicted trypsin digest pattern (ExPASY program Peptide Mass) of Apoptin revealed that the T cluster at 106-108 and the single T at position 114 reside on different tryptic peptides. In order to distinguish between these two loci, we performed tryptic phosphopeptide mapping of P-Apoptin derived from Saos-2 cells. We found that only one major tryptic fragment was phosphorylated. On a very long exposure, several other faint spots were also detected, but because the signal ratio of the major spot is so extremely high compared to the faint spots, they probably do not represent relevant sites, or, alternatively, may be derived from the proposed cellular contaminant also seen in PAA.

With this assumption, taken together with the GFP-deletion mutant results, the presence of only one major phosphorylated peptide suggests that Apoptin is phosphorylated either within the triple-T stretch or on the lone T, but not in both loci.

6. Phosphorylation Occurs within the Triple-T Locus (106-108)

In order to pinpoint finally which loci contained the phosphorylation site, as well as to rule out the formal possibility of minor involvement of other residues between position 80 and 121, we used the in vivo phosphorylation assay to analyze a series of 5-alanine scanning mutants, which encode a protein that has every five residues in the Apoptin gene replaced by five alanines (FIG. 3). Of particular interest were mutants Ala(5)-106 (SEQ ID NO:7), in which T106-108 are all replaced by alanines, and Ala(5)-111 (SEQ ID NO:8), in which T-114 is also replaced. We tested all mutants between 86-115 in the in vivo phosphorylation assay. (Unfortunately, the mutants between 80 and 85 could not be tested in the assay because this mutation abolishes the immunoprecipitation epitope). Some of the mutants migrated as doublets. Because the lowest band was closer in migration to wild-type Apoptin and was also universally present, we assumed that the lower band was the significant band. In these experiments, all constructs were expressed at roughly equal levels, as determined by immunostaining the PVDF membrane post-autorad analysis. Most of the alanine mutants tested were robustly phosphorylated, including Ala (5)-111 (SEQ ID NO:8), suggesting that the lone T at position 114 is not involved in phosphorylation. In contrast, the Ala(5)-106 mutant (SEQ ID NO:7) showed total or almost total absence of phosphorylation in multiple experiments, suggesting that this mutation abolishes a major phosphorylation site.

In conclusion, these data are consistent with a triple-T locus (106-108) representing a major tumor-specific phosphorylation locus of Apoptin.

7. Single Point Mutants Confirm the Triple-T Locus is a Major Phosphorylation Site of Apoptin Because the Triple-T locus is contained on only one tryptic fragment, it became necessary to further dissect the phosphorylation site using point mutation, replacing the suspected threonine residues in turn with alanine residues, which are unable to be phosphorylated by a kinase. These studies could help to determine not only the modified site, but also which surrounding amino acids are required for efficient phosphorylation; in order to maintain specificity, threonine kinases require not only a threonine to phosphorylate, but also a surrounding context of amino acids, known as a consensus site. A possible caveat to point mutational studies around a consensus site is that replacing an amino acid with an alanine residue might abolish phosphorylation, not because that replaced residue was the modified site itself, but rather because it formed part of a surrounding consensus site. Another possible caveat around these studies can be that in a stretch of multiple identical phosphorylatable residues (such as the triple-T locus), the consensus might be so loose that replacement of the threonine that is phosphorylated in vivo might result in the kinase phosphorylating the adjacent threonine instead, which may probably not occur in the wild-type situation. Thus, the act of studying the consensus site by changing residues can actually change the reality of the phenomenon.

Keeping these well-known caveats in mind, we proceeded with point mutational analyses. In order to demonstrate conclusively that the Triple-T locus contains a major phosphorylation site of Apoptin, we generated single point mutants, replacing T106 (SEQ ID NO:10), T107 and T108 with an alanine, which cannot be phosphorylated. In addition, because there is a common family of kinases, known as the proline-directed kinases, that requires a proline directly downstream of the phosphorylation site (Ishida et al., 2000), we also replaced P109 with an alanine (see, FIG. 4 for a summary of these constructs). The mutants were called, respectively, T106A (SEQ ID NO:10), T107A (SEQ ID NO:11), T108A (SEQ ID NO:12), and P109A (SEQ ID NO:13). Each of these constructs was transfected into Saos-2 cells, along with an empty vector and CMV-Vp3 controls, and subjected to the in vivo phosphorylation assay. In one of a series of experiments, T108A (SEQ ID NO:12) and CMV-Vp3 were still phosphorylated, T107A (SEQ ID NO:11) and P109A (SEQ ID NO:13) were not. T106A (SEQ ID NO:10) was faintly phosphorylated. Western blot analysis confirmed that all constructs were expressed at roughly equal levels. These results suggested that both T106 and T107 are necessary for Apoptin phosphorylation. Furthermore, the result with the P109A (SEQ ID NO:13) mutant suggests that the phosphorylation site resides within a consensus site of defined conformation, possibly mediated by a proline-directed kinase. In repeated experiments we also saw that the T108A (SEQ ID NO:12) mutation resulted in impaired or abolished phosphorylation of the Triple-T locus, suggesting that this site also is involved either in the modification itself or in preserving the consensus site.

To analyze the consensus site requirements further, we tested three additional double alanine mutants in the same assay: T106A107A (SEQ ID NO:17); T107A108A (SEQ ID NO:18), and T106A108A (SEQ ID NO:19) (FIG. 4). Consistent with sequence context being important for efficient phosphorylation, all three of these constructs were phosphorylated poorly or not at all.

Thus, we concluded that T106, T107 and T108 are either all three phosphorylated, or only one or two are and the other site(s) is/are a necessary part of the kinase consensus sequence. Whichever is the case, all three residues seem to be essential for the complete phenomenon, as is P109. To finally pinpoint the site, we had to use another technique: mass spectrometric analysis of the wild-type phosphorylation site (see next section).

8. Mass Spectrometric Analysis Shows that Apoptin is Phosphorylated on T108 In Vitro Recombinant Apoptin protein GST-Apoptin was subjected to in vitro phosphorylation by lysates from Saos-2 tumor cells as described above, purified, and submitted to several procedures, namely, matrix-assisted laser desorption/ionization (MALDI) analysis and electrospray ionization collision-induced dissociation (ESI-CID) to assign the phosphorylated modification to a particular amino acid residue. These experiments clearly showed that T108 was the phosphorylation site under these conditions.

Taking together the in vivo point mutation data along with the in vitro data described here, it is shown that T108 is the phosphorylation site, whereas T106, T107 and P109 are important for maintaining the conformation and recognition sequences for the kinase consensus site.

9. Phosphospecific Apoptin Antibodies Confirm that Apoptin is Phosphorylated on T108 In Vivo Another way to study the wild-type modifications of Apoptin is to detect such events in vivo with a specific antibody, which in addition can be used for a wide variety of other purposes, including diagnostics. To this end, Eurogentec generated phosphospecific antibodies (PSA) for Apoptin. Rabbits were injected with peptides synthetically phosphorylated either on T106, T107 or T108. The sera of all rabbits gave a high titer of reactivity against the injected phosphopeptide, but these sera were a mixed population of phosphospecific (PSA)- and non-phosphospecific (NPSA)-reacting antibodies, as expected. In order to separate the two activities, a double purification step was performed using phospho- and non-phosphopeptide columns. The resultant PSA and NPSA purified antisera were confirmed by competitive ELISA with the phospho- and non-phosphopeptides by Eurogentec using standard procedures. We confirmed the PSA or NPSA recognition status of the antibodies by Western blot. Specifically, Saos-2 cells were transfected with wild-type CMV-Vp3, lysed and subjected to Western blot analysis with each of the three PSAs, 106-P, 107-P and 108-P. As a control, bacterially produced Apoptin or Apoptin transfected into VH10 normal cells was also included in the Western blot analysis.

As expected from the mass spectrometric analysis in vitro, antibody 108-P PSA behaved as a true Apoptin phosphospecific antibody in vivo. Specifically, transfected Apoptin derived from living Saos-2 cultures was strongly detectable by the 108-P antibody in Western blot. In contrast, recombinant bacterial MPB-Vp3, which cannot be phosphorylated in bacteria, was completely negative, confirming that the 108-P antibody recognizes the phosphorylation moiety as its epitope. In contrast, Apoptin transfected in vivo into normal VH10 cells showed only very faint signal with the 108-P antibody, which is consistent with the radioactive in vitro kinase assay reported in results section 2. Nevertheless, this signal in VH10 cells was at least, as in vitro, more than 50-200 times less intense than in tumor cells. As a control, both 111.3 general anti-Apoptin antibody and 108-X, the corresponding non-phosphospecific antibody, equally recognized Saos-2-derived Apoptin, VH10-derived Apoptin, and bacterial MBP-Vp3, proving that 108-P is a true phosphospecific antibody. These data further support the idea that T108 is indeed the phosphorylated residue in vivo on wild-type Apoptin protein.

In contrast, the putative PSAs 106-P and 107-P did not behave as true phosphospecific Apoptin antibodies in the same Western analysis. Specifically, there was no true difference between 106-P and 106-X, nor between 107-P and 107-X, and 111.3, which recognizes Apoptin regardless of its phosphorylation state. These results suggest that while the rabbits were competent to immunologically react against peptides artificially phosphorylated on residues 106 and 107, these epitopes do not actually exist in vivo in cells transfected with Apoptin. Thus, the status of T108 as the phosphorylation site is further bolstered by these data.

Another application of the phosphospecific antibody is to determine whether the Apoptin protein is phosphorylated in chicken anemia virus-infected transformed chicken cells in vivo. For this, we exploited the 108-P antibody Western blot technique. We compared lysates from CAV-infected MDCC-MSB 1 cells with lysates prepared from 293T transformed human cells transfected with CMV-Vp3 plasmid. Although there was a roughly equal amount of Apoptin protein in both samples, the CAV-derived Apoptin protein was far more phosphorylated, as measured by the 108-P antibody (>20-50×). Such a stoichiometric hyperphosphorylation may stem from chicken cells having more kinase activity, from CAV infection stimulating the kinase pathway, or from facilitation by the other CAV proteins VP1 and/or VP2. These results strengthen the idea that Apoptin phosphorylation on T108 occurs in vivo in a natural CAV setting, and in transformed cells of its natural tropism (chicken T lymphocytes) under circumstances in which Apoptin-induced apoptosis occurs.

A further application of phosphospecific antibodies is to achieve a nonradioactive in vitro kinase assay, in which the reactions are performed with nonradioactive ATP and Western blot analyzed with the 108-P antibody or subjected to 108-P ELISA or other possible assays. Using the Western blot approach, we confirmed the presence of T108 phosphorylating activity within lysates of Jurkat T cells, EBV-transformed LCL cells, U2OS and Soas-2 cells, but not in lysates of CD31- normal diploid fibroblasts or synoviocytes derived from bone fractures of otherwise healthy patients.

The 108-P antibody is also very useful in immunofluorescence analyses in tumor and normal cells transfected with wild-type CMV-Vp3. In this case, the ectopic Apoptin protein was double-labeled with 111.3, detected with fluorescein-conjugated secondary antibody and 108-P, and detected with rhodamine-conjugated secondary antibody. Using this strategy, the entire pool of Apoptin should be labeled in green, regardless of its phosphorylation state, whereas only the phosphorylated Apoptin should also be detectable in red.

When this analysis was performed in tumor cells, it became clear that the two antibodies had overlapping but distinct recognition patterns. In tumor cells, 111.3 recognizes total Apoptin, which is distributed at early times in the cytoplasm and at later times accumulates in the nucleus and in blobs around the edges of the nucleus. Also at later times, very distinct, round bodies within the nucleus are also frequently seen. When the same cells were examined in the red channel for phosphorylation-specific signal, several things became apparent: 1) only a subset of Apoptin is recognized by the PSA 108-P; 2) 108-P is more likely to recognize Apoptin in the nucleus, although in a minority of cases cytoplasmic Apoptin was also positive with 108-P; and 3) very intriguingly, the distinct, round bodies in the nucleus are not recognized by 108-P. These data suggest that not all Apoptin is phosphorylated at any one time in a tumor cell, that phosphorylation is more commonly maintained in the nucleus, and that Apoptin is dephosphorylated in the round subnuclear bodies. A model to explain these results is that Apoptin becomes phosphorylated gradually in the cytoplasm; as a result, it is able to translocate to the nucleus. Then, it must become dephosphorylated to enter the subnuclear bodies. Such localization differences therefore support the data, seen in the gain-of-function studies, that the phosphorylation has relevance for Apoptin function.

We repeated the analysis with 107-P and 106-P, but these antibodies exhibited the same staining as the basal Apoptin antibody 111.3, consistent with the idea that they are not true PSAs. To rule out the trivial possibility that the epitope around the triple-T locus, regardless of modification, distinguishes itself from the N-terminal 111.3 epitope, we repeated the immunofluorescence with the NPSA, 108-X. However, the staining of this antibody coincided completely with that of 111.3, including in the cytoplasm and in the round sub-nuclear bodies, confirming that the difference in localization of the 108-P- and 111.3-detectable pools of Apoptin is due solely to the phosphorylated residue on T-108.

10. A diagnostic cancer or related aberrancy assay based on Apoptin PSA 108-P

The marked specificity of 108-P for Apoptin resident in tumor or transformed cells, coupled with the ability to use recombinant Apoptin easily in an in vitro kinase assay, led us to develop an aberrant-specific ELISA assay, hereafter to be referred to as ApoCheck™. Such an assay or kit is useful both for research and clinical diagnosis and is based on immunological detection of the phosphate modification present on in vitro reacted Apoptin protein or Apoptin-based peptide. As an example, which is not limiting the present invention, we used MBP-Vp3 recombinant protein as a substrate in the non-radioactive in vitro kinase assay.

Using ApoCheck with the antibody 108-P, we were able to detect kinase activity very strongly in reactions performed with Saos-2 lysates. In contrast, kinase activity was scarcely detectable in reactions performed with CD31- normal fibroblast lysates. In the dilution series, Saos-2 signal exceeded CD31- signal by a robust, at least ten-fold difference in titer.

In contrast, ApoCheck using 107-P and 106-P antibodies in place of 108-P gave no difference in signal between Saos-2- and CD31-reacted substrate. These data are consistent with T-108 being the in vitro phosphorylated residue by Saos-2, as already shown by mass spectrometry and 108-P Western blotting experiments.

To confirm the specificity of the ELISA for phosphorylated epitope, we repeated the 108-P ELISA as described above except that we performed a competition by pretreating the lysates with a 200× molar excess of the phosphorylated peptide. As expected, the competition resulted in loss of specific signal down to the background level. Thus, the signal provided by Saos-2 cell lysates is dependent upon the phosphorylated T-108 epitope.

Our data show that ApoCheck specifically detects phosphorylated Apoptin. Taken together with all other disclosed data, including detection of phosphorylated Apoptin in frozen human tumor samples, we have shown that ApoCheck is a useful diagnostic tool for the identification of phosphorylated Apoptin in, for example, tumorous or suspect patient material.

11. Evidence for a Distal Locus Influencing the Phosphorylation of Apoptin

Interestingly, the Ala(5)-91 mutant (SEQ ID NO:4) (see FIG. 3) reproducibly showed phosphorylation that was significantly reduced. Given that replacing residues 106-110 with alanines almost completely abolished Apoptin phosphorylation, whereas replacing residues 91-96 with alanines only impaired the phosphorylation somewhat, the most likely explanation is that the domain encompassed by 91-96 represents a facilitator of phosphorylation at the main triple-T locus. In contrast, if 91-96 merely represented a minor phosphorylation site, the triple-T knockout mutant should be more phosphorylated, and it is not. Indeed, mass spectrometric analysis confirmed that the 91-96 locus is not itself phosphorylated. The presence of a phosphorylation-inducing domain in this locus is consistent with the fact that the GFP-100-121 mutant was reproducibly hypophosphorylated with respect to the other C-terminal fragments.

Taken together, these data are consistent with a model wherein the triple-T locus (threonines 106-108) contains a major tumor-specific phosphorylation site of Apoptin, whereas there might be a facilitator of phosphorylation within positions 91-95.

12. Apoptin Phosphorylation within the Triple-T Locus is Necessary for Apoptosis Induction in Tumor cells In order to determine the functionality of tumor-specific phosphorylation of Apoptin, we tested whether the described alanine point replacement mutants could still induce apoptosis in tumor cells. In addition, we also prepared and tested mutants containing glutamic acid replacements at the key residues T106, T107, T108 (see, FIG. 4) and as a control LacZ. Glutamic acid is widely used to confer gain-of-function for mutated phosphorylation sites because the negative charge of this amino acid emulates the negative charge of the phosphorylation modification (Maciejewski et al., 1995). Note that the negative charge of the glutamic acid may be able to spread its effects to adjacent sites.

We inspected Saos-2 cells three to five days after transfection using immunofluorescence analysis. Cells expressing Apoptin constructs were scored as apoptotic if they contained a completely condensed, apoptotic nucleus. Wild-type Apoptin was able to kill tumor cells to a level that will be referred to here as the baseline level. In contrast, in one of a series of experiments, mutants T106A (SEQ ID NO:10), T107A (SEQ ID NO:11), and P109A (SEQ ID NO:13) induced reduced death compared to the baseline. Strikingly, the T106E (SEQ ID NO:14) and T107E (SEQ ID NO:15) mutants demonstrated a gain-of-function phenotype, in that the apoptosis induced was restored back to baseline levels by the glutamic acid substitution. In the same experiment, T108A (SEQ ID NO:12) and T108E (SEQ ID NO:16) mutants exhibited only baseline death. Thus there seemed to be no correlation between the phosphorylation status of the mutant and the ability of that mutant to kill. Therefore, we repeated these experiments more extensively, with larger numbers of cells, and found that T108A (SEQ ID NO:12), along with T107A (SEQ ID NO:11), T106A (SEQ ID NO:10) and P109A (SEQ ID NO:13), did also show reduced death activity compared to Apoptin, whereas T108E (SEQ ID NO:16), along with T107E (SEQ ID NO:15) and T106E (SEQ ID NO:14), did also show baseline activity.

Taking together a number of experiments, the results are summarized as follows: all alanine replacements in the region of the Triple-T locus caused an impairment in apoptosis, though did not abolish it completely. Similarly, all glutamic acid replacements in the area were able to restore the death to baseline or slightly above baseline activity.

These results strongly support the hypothesis that phosphorylation occurs within the triple-T locus (T106-T107-T108) and that this phosphorylation is necessary for the apoptotic function of Apoptin.

13. Apoptin Phosphorylation within the Triple-T Locus is Sufficient for Apoptosis Induction in Normal Cells In order to determine the functionality of tumor-specific phosphorylation of Apoptin, we tested whether the glutamic acid point replacement mutants described above could confer gain-of-function in normal cells. Specifically, we wanted to determine the effect of a mutation that mimicked constitutive phosphorylation on the ability of Apoptin to translocate to the nucleus and induce apoptosis in normal cells. To this end, we transfected T106E (SEQ ID NO:14), T107E (SEQ ID NO:15), T108E (SEQ ID NO:16), wild-type CMV-Vp3 and the negative control plasmid encoding LacZ-myc into human CD31- fibroblasts and mesenchymal stem cells and performed immunofluorescence analysis, as described above, with anti-Apoptin antibodies and DAPI staining of the nucleus. These studies showed that replacement of any of the three threonines of the triple-T locus was sufficient to cause Apoptin to enter the nucleus and induce apoptosis in the majority of cells transduced. T108E (SEQ ID NO:16) demonstrated slightly more activity than T107E (SEQ ID NO:15), which in turn demonstrated slightly more activity than did T106E (SEQ ID NO:14). In contrast, wild-type Apoptin remained primarily in the cytoplasm and did not induce apoptosis. As an additional control, a representative single reduced-activity alanine mutant, T107A (SEQ ID NO:11), was just as inert in this assay as was wild-type Apoptin, and LacZ-myc and did not induce apoptosis either.

Next, we generated and tested a representative gain-of-function MBP-Vp3 recombinant protein (MBP-Vp3T107E, with the centre of the Triple-T locus mutated to a negatively charged glutamic acid versus MBP-Vp3 and MBP proteins in cytoplasmic microinjection experiments in normal human mesenchymal stem cells and VH10 normal fibroblasts. Similar to the studies with DNA mutants, the MBP-Vp3T107E protein exhibited a gain-of-function phenotype; in other words, it was able to translocate to the nucleus and induce apoptosis in normal cells, whereas MBP and MBP-Vp3 remained in the cytoplasm and did not kill.

These results suggest that any negative charge (and by extension, phosphorylation event) in the triple-T locus is sufficient to confer upon Apoptin the ability to go to the nucleus and induce apoptosis in an aberrant-independent manner. By inference, such a gain-of-function phenotype implies that, under the typical, wild-type situation in a tumor cell, the aberrant-specific phosphorylation event is relevant for Apoptin's aberrant-specific apoptosis ability.

Thus, we have shown that the Triple-T locus itself is the key area mediating phosphorylation, most usually on position T108, although the entire sequence context from 106 to 109 is clearly involved in its regulation, along with other regions of the protein (e.g., 91-96).

14. Domains Influencing Nuclear Import and Activity of Apoptin

We noticed that the Ala(5)-91 mutant (SEQ ID NO:4) was severely impaired for nuclear import, as were the Ala(5)-81 mutant and Ala(5)-86 mutant (SEQ ID NO:3). Furthermore, a GFP-100-121 fusion protein containing the C-terminal 22 amino acids of Apoptin did not accumulate in the nucleus, whereas a GFP-80-121 fusion protein containing the C-terminal 42 amino acids of Apoptin clearly did. In addition, the GFP-80-121 fusion protein also induced apoptotic activity in human tumor cells, such as Saos-2 cells.

The below-depicted Table 1 summarizes the results of the nuclear localization and induction of apoptosis by GFP-Vp3 fusion proteins or Apoptin Ala-mutants. Both the GFP-Vp3 and Apoptin Ala mutants have been described in FIG. 2 and FIG. 3, respectively.

TABLE 1

| | Apoptin | |
|---|---|---|
| DNA-construct | nuclear localization | apoptosis |
| GFP-Vp3 | Yes | Yes |
| GFP-1-69 | No | No |
| GFP-70-121 | Yes | Yes |
| GFP-80-121 | Yes | Yes |
| GFP-100-121 | No | No |
| NLS-Vp3-1-69 | Yes | Yes |
| Ala(5)-81 | No | ND |
| Ala(5)-85 | No | ND |
| Ala(5)-91 | No | ND |
| wild-type Vp3 | Yes | ND |

ND not determined

Taken together these data with the phosphorylation data, it appears that the amino acids 80 to 121 comprise at least 3 key elements crucial for tumor-specific activity: nuclear import domain(s), phosphorylation within the triple-T locus, and a domain facilitating the phosphorylation. The key elements will, for example, be essential to identify a universal mediator of phosphorylation in human tumor cells. Interfering with this mediator could provide a new anti-cancer therapy.

REFERENCES

Baker, S. J., Markowitz, S., Fearon, E. R., Willson, J. K. V., and Vogelstein, B. (1990). Suppression of human colorectal carcinoma cell growth by wild-type p53. Science 249, 912-915.

Bellamy, C. O. C., Malcomson, R. D. G., Harrison, D. J., and Wyllie, H. (1995). Cell death and disease: The biology and regulation of apoptosis. Seminars in Cancer Biology 6, 3-12.

Blaydes, J. P., Vojtesek, B., Bloomberg, G. B., and Hupp, T. R. (2000). The development and use of phospho-specific antibodies to study protein phosphorylation. Methods Mol Biol 99, 177-89.

Danen-Van Oorschot, A. A. A. M., Fischer, D. F., Grimbergen, J. M., Klein, B., Zhuang, S.-M., Falkenburg, J. H. F., Backendorf, C., Quax, P. H. A., Van der Eb, J. A., and Noteborn, M. H. M. (1997). Apoptin induces apoptosis in human transformed and malignant cells but not in normal cells. Proceedings National Academy Sciences, USA: 94, 5843-5847.

Danen-Van Oorschot, A. A. A. M, Den Hollander, A., Takayama, S., Reed, J., Van der Eb, A. J. and Notebom, M. H. M. (1997a). BAG-1 inhibits p53-induced but not Apoptin-induced apoptosis. Apoptosis 2, 395-402.

Duke, R. C., Ocjius, D. M., Young, J, D-E. (1996). Cell suicide in health and disease. Scientific American, December 1996, 48-55.

Diller, L., Kassel, J., Nelson, C., Gryka, M. A., Litwak, G., Gebhardt, M., Bressac, B., Ozturk, M., Baker, S. J., Vogelstein, B., and Friend, S. H. (1990). p53 functions as a cell cycle control protein in osteosarcomas. Molecular Cellular Biology 10, 5772-5781.

Earnshaw, W. C., 1995. Nuclear changes in apoptosis. Current Opinion in Cell Biology 7, 337-343.

Evan G. I., Lewis G. K., Ramsay G., Bishop J. M., (1985) Isolation of monoclonal antibodies specific for human c-myc proto-oncogene product. Mol Cell Biol Dec; 5(12): 3610-3616.

Friedlander, P., Haupt, Y., Prives, C., and Oren, M. (1996). A mutant p53 that discriminates between p53-responsive genes cannot induce apoptosis. Mol Cell Biol 16(9): 4961-4971.

Harlow, E. and Lane, D. Antibodies: A Laboratory Manual (1988). 1988 Cold Spring Harbor Laboratory Press, New York. Chapter 14, “Immunoassay”, pp. 553-612.

Hockenberry, D. M. (1994). Bcl-2 in cancer, development and apoptosis. Journal of Cell Science, Supplement 18, 51-55.

Ishida, N., Kitagawa, S., Hatakeyama, S., and Nakayama, K. (2000). Phosphorylation at serine 10, a major phosphorylation site of p27(Kipl), increases its own stability. J Biol. Chem. 275(33):25146-54.

Kerr, J. F. R., Winterford, C. M., and Harmon, B. V. (1994). Apoptosis: Its significance in cancer and cancer therapy. Cancer 73, 2013-2026.

Levine, A. J. (1997). p53, the cellular gatekeeper for growth and division. Cell 88, 323-331.

Maciejewski P. M., Peterson F. C., Anderson P. J., Brooks C. L. (1995) Mutation of serine 90 to glutamic acid mimics phosphorylation of bovine prolactin (1995) J Biol Chem; 270(46):27661-5

Maniatis, T., Fritsch, E. F., and Sambrook, J. (1982). Molecular Cloning: A Laboratory Manual. CSHL Press, New York, USA.

McDonell T. J., Meyn, R. E., Robertson, L. E. (1995). Implications of apoptotic cell death regulation in cancer therapy. Seminars in Cancer Biology 6, 53-60.

Noteborn, M. H. M. (1996). PCT application WO 96/41191. Methods and Uses for Apoptin. Noteborn, M. H. M. and Danen-Van Oorschot, A. A. A. M. (1998). PCT application 98/00688, Methods and Means for Inducing Apoptosis by Interfering with Bip-like Proteins, PCT International Publication WO 99/28461.

Noteborn, M. H. M., and De Boer, G. F. (1996). U.S. Pat. No. 5,491,073 Cloning of chicken anemia DNA.

Noteborn, M. H. M., De Boer, G. F., Van Roozelaar, D., Karreman, C., Kranenburg, O., Vos, J., Jeurissen, S., Zantema, A., Hoeben, R., Koch, G., Van Ormondt, H., and Van der Eb, A. J. (1991). Characterization of cloned chicken anemia virus DNA that contains all elements for the infectious replication cycle. Journal of Virology 65, 3131-3139.

Noteborn, M. H. M., and Pietersen, A. (1998). A gene delivery vehicle expressing the apoptosis-inducing proteins VP2 and/or Apoptin. PCT Application no. PCT/NL98/00213, International Patent Publication WO 98/46760.

Noteborn, M. H. M., Todd, D., Verschueren, C. A. J., De Gauw, H. W. F. M., Curran, W. L., Veldkamp, S., Douglas, A. J., McNulty, M. S., Van der Eb, A. J., and Koch, G. (1994). A single chicken anemia virus protein induces apoptosis. Journal of Virology 68, 346-351.

Noteborn, M. H. M., and Zhang, Y. (1998) “Determining the Transforming Capability of Agents”, International Patent Publication WO 99/08108, PCT Application no. PCT/NL98/00457.

Noteborn, M. H. M., Danen-Van Oorschot, A. A. A. M., Van der Eb, A. J. (1998a). Chicken anemia virus: Induction of apoptosis by a single protein of a single-stranded DNA virus, Seminars in Virology 8, 497-504.

Noteborn M. H. M., Zhang, Y.-H. and Van der Eb, A. J. (1998b). Viral protein Apoptin induces apoptosis in tumor cells and after UV-treatment in untransformed cells from cancer-prone individuals: A review. Mutation Research 400, 447-456.

Noteborn, M. H. M. (1999). Apoptin-induced apoptosis: a review. Apoptosis 4, 317-319.

Noteborn et al., Gene 233 (1998) 165-172

Paulovich, A. G., Toczyski, D., Hartwell, H. (1997). When checkpoints fail. Cell 88, 315-321.

Pietersen, A. M., Van der Eb, M. M., Rademaker, H. J., Van den Wollenberg, D. J. M., Rabelink, M. J. W. E., Kuppen, P. J. K., Van Dierendonck, J. H., Van Ormondt, H., Masman, D., Van de Velde, C. J. H., Van der Eb, Hoeben, R. C., and Noteborn, M. H. M. (1999). Specific tumor-cell killing with adenovirus vectors containing the Apoptin gene. Gene Therapy 6, 882-892.

Sachs, L. and Lotem, J. (1993). Control of programmed cell death in normal and leukemia cells: New implications for therapy. Blood 82, 15-21.

Sanger, F., Nicklen, S., and Coulsen, A. R. (1977). DNA sequencing with chain-terminating inhibitors. Proceedings National Academic Sciences USA 74, 5463-5467.

Steller, H. (1995). Mechanisms and genes of cellular suicide. Science 267, 1445-1449.

Telford, W. G., King, L. E., Fraker, P. J. (1992). Comparative evaluation of several DNA binding dyes in the detection of apoptosis-associated chromatin degradation by flow cytometry. Cytometry 13, 137-143.

Teodoro, J. G. and Branton, P. E. (1997). Regulation of apoptosis by viral gene products. Journal of Virology 71, 1739-1746.

Thompson, C. B. (1995). Apoptosis in the pathogenesis and treatment of disease. Science 267, 1456-1462.

White, E. (1996). Life, death, and the pursuit of apoptosis. Genes and development 10, 1-15.

Wyllie, A. H. (1995). The genetic regulation of apoptosis. Current Opinion in Genetics and Development 5, 97-104.

Wyllie, A. H., Kerr, J. F. R., Currie, A. R. (1980). Cell death: The significance of apoptosis. International Review of Cytology 68, 251-306.

Yuasa, N. (1983). Propagation and infectivity titration of the Gifu-1 strain of chicken anaemia agent in a cell line [MDCC-MSB1] derived from Marek’s disease lymphoma. Nat’l. Inst. Anim. Health Q. 23:12-20

Zhuang, S.-M., Landegent, J. E., Verschueren, C. A. J., Falkenburg, J. H. F., Van Ormondt, H., Van der Eb, A. J., Noteborn, M. H. M. (1995). Apoptin, a protein encoded by chicken anemia virus, induces cell death in various human hematologic malignant cells in vitro. Leukemia9 S1, 118-120.

Zhuang, S.-M., Shvarts, A., Van Ormondt, H., Jochemsen, A.-G., Van der Eb, A. J., Noteborn, M. H. M. (1995a). Apoptin, a protein derived from chicken anemia virus, induces a p53-independent apoptosis in human osteosarcoma cells. Cancer Research 55, 486-489.

The invention claimed is:

1. A vector comprising a nucleic acid encoding Apoptin or a functional fragment thereof, wherein said Apoptin is provided with a mutation that mimics constitutive phosphorylation on a threonine residue and wherein said threonine residue, in the Apoptin of FIG. 1 (SEQ ID NO:1), resides at amino acid position 108.

2. A gene delivery vehicle comprising the vector of claim 1.

3. A host cell comprising the vector of claim 1.

4. A vector comprising a nucleic acid encoding Apoptin of SEQ ID NO:1, wherein said Apoptin comprises replacement of at least one threonine residue located at amino acid position 106, 107, or 108 of SEQ ID NO:1 with a glutamic acid to mimic constitutive phosphorylation.

5. A gene delivery vehicle comprising the vector of claim 4.

6. A host cell comprising the vector of claim 4.

7. A vector comprising a nucleic acid encoding a protein comprising SEQ ID NO:1 with a mutation of amino acid position 108 that mimics constitutive phosphorylation of a threonine residue.

* * * * *

UNITED STATES PATENT AND TRADEMARK OFFICE

CERTIFICATE OF CORRECTION

PATENT NO. : 7,319,034 B2 Page 1 of 1
APPLICATION NO. : 10/083849
DATED : January 15, 2008
INVENTOR(S) : Mathieu Hubertus Maria Noteborn et al.

It is certified that error appears in the above-identified patent and that said Letters Patent is hereby corrected as shown below:

| | | |
|---|---|---|
| COLUMN 2, | LINE 2, | change “Notebom et al.,” to --Noteborn et al.,-- |
| COLUMN 2, | LINE 21, | change “Notebom,” to --Noteborn,-- |
| COLUMN 8, | LINE 2, | change “thecleavedPCR” to --the cleaved PCR-- |
| COLUMN 10, | LINE 38, | change “keratinocytes Were a” to --keratinocytes were a-- |
| COLUMN 10, | LINE 55, | change “Dr. T. Huizing a,” to --Dr. T. Huizinga,-- |
| COLUMN 10, | LINES 60-61, | change “MDCC-MSB 1” to --MDCC-MSB1-- |
| COLUMN 11, | LINE 28, | change “PERMANOXT” to --PERMANOX™-- |
| COLUMN 13, | LINE 16, | change “Phospholmage” to --PhosphoImage-- |
| COLUMN 13, | LINE 39, | change “RuterLeliveld,” to --Ruter Leliveld,-- |
| COLUMN 16, | LINE 51, | change “performedjust” to --performed just-- |
| COLUMN 22, | LINES 40-41, | change “MDCC-MSB 1” to --MDCC-MSB1-- |
| COLUMN 27, | LINE 7, | change “Notebom,” to --Noteborn,-- |
| COLUMN 29 | LINE 5, | change “Leukemia9” to --Leukemia 9-- |

Signed and Sealed this

Thirtieth Day of September, 2008

JON W. DUDAS
*Director of the United States Patent and Trademark Office*